United States Patent
Patel

(10) Patent No.: US 11,634,436 B2
(45) Date of Patent: Apr. 25, 2023

(54) PYRIDINE LACTAM COMPOUNDS AND METHODS OF USE THEREOF

(71) Applicant: Genentech, Inc., South San Francisco, CA (US)

(72) Inventor: Snahel Patel, South San Francisco, CA (US)

(73) Assignee: Genentech, Inc., South San Francisco, CA (US)

(*) Notice: Subject to any disclaimer, the term of this patent is extended or adjusted under 35 U.S.C. 154(b) by 105 days.

(21) Appl. No.: 17/067,638

(22) Filed: Oct. 9, 2020

(65) Prior Publication Data

US 2021/0032271 A1 Feb. 4, 2021

Related U.S. Application Data

(63) Continuation of application No. PCT/US2019/028011, filed on Apr. 18, 2019.

(60) Provisional application No. 62/660,397, filed on Apr. 20, 2018.

(51) Int. Cl.

| C07D 519/00 | (2006.01) |
|---|---|
| A61P 1/04 | (2006.01) |
| A61P 9/10 | (2006.01) |
| A61P 11/00 | (2006.01) |
| A61P 13/12 | (2006.01) |
| A61P 17/06 | (2006.01) |
| A61P 25/16 | (2006.01) |
| A61P 25/28 | (2006.01) |
| C07D 498/04 | (2006.01) |
| C07D 471/04 | (2006.01) |
| C07D 487/04 | (2006.01) |

(52) U.S. Cl.
CPC ........ *C07D 519/00* (2013.01); *C07B 2200/05* (2013.01)

(58) Field of Classification Search
CPC .. C07D 519/00; C07D 498/04; C07D 471/04; C07D 487/04; C07D 519/05; C07B 2200/05; A61P 1/04; A61P 9/10; A61P 11/00; A61P 13/12; A61P 17/06; A61P 25/16; A61P 25/28; A61P 17/16
See application file for complete search history.

(56) References Cited

U.S. PATENT DOCUMENTS

| 5,206,234 A | 4/1993 | Bock et al. |
|---|---|---|
| 6,350,741 B1 | 2/2002 | Golec et al. |
| 7,057,046 B2 | 6/2006 | Sher et al. |
| 7,425,550 B2 | 9/2008 | Sher et al. |
| 9,815,850 B2 | 11/2017 | Estrada et al. |
| 11,072,607 B2 * | 7/2021 | Patel ............... A61P 13/12 |
| 2004/0002495 A1 | 1/2004 | Sher et al. |
| 2011/0038877 A1 | 2/2011 | Way et al. |
| 2017/0008877 A1 | 1/2017 | Patel et al. |
| 2018/0170927 A1 | 6/2018 | Patel et al. |

FOREIGN PATENT DOCUMENTS

| EP | 3318267 A1 | 5/2018 | |
|---|---|---|---|
| WO | 02/20530 A1 | 3/2002 | |
| WO | 03/046222 A1 | 6/2003 | |
| WO | 2004/037986 A2 | 5/2004 | |
| WO | 2006/031606 A2 | 3/2006 | |
| WO | 2008/011190 A1 | 1/2008 | |
| WO | 2009/140128 A2 | 11/2009 | |
| WO | 2013/059791 A2 | 4/2013 | |
| WO | 2014/009495 A1 | 1/2014 | |
| WO | 2014/023708 A1 | 2/2014 | |
| WO | 2014/125444 A1 | 8/2014 | |
| WO | 2014/145022 A1 | 9/2014 | |
| WO | 2014/170892 A1 | 10/2014 | |
| WO | 2016/027253 A1 | 2/2016 | |
| WO | 2017/001645 A1 | 1/2017 | |
| WO | 2017/001655 A1 | 1/2017 | |
| WO | 2017/001660 A1 | 1/2017 | |
| WO | WO-2017004500 A1 * | 1/2017 | ............. A61K 31/55 |
| WO | 2017/096301 A1 | 6/2017 | |
| WO | 2017/103851 A1 | 6/2017 | |

(Continued)

OTHER PUBLICATIONS

Huntington Dis Symptoms and causes—1998-2022 Mayo Clinic. pdf.*
National Institute of Diabetes and Digestive and Kidney Diseases, Preventing Chronic Kidney Disease, obtained from https://www.niddk.nih.gov/health-information/kidney-disease/chronic-kidney-disease-ckd/prevention on Jan. 21, 2019 (Year: 2019).*
Bertrand, M., et al., "cIAPI and cIAP2 facilitate cancel cell survival by functioning as E3 ligases that promote RIP1 ubiquitination" MOL CELL 30(6):689-700 (Jun. 20, 2008).
Chen, Z., "Ubiquitination in Signaling to and Activation of IKK" Immunol Rev 246(1):95-106 (Mar. 21, 2012).

(Continued)

*Primary Examiner* — John M Mauro
(74) *Attorney, Agent, or Firm* — Jelena Libby

(57) ABSTRACT

The invention provides compounds having the general formula I:

or pharmaceutically acceptable salts thereof, wherein X, Y, $R^1$, $R^2$, $R^{7a}$, $R^{7b}$, X, $R^{B1}$, $R^{B2}$, n, p, q, the A ring and the B ring are as described herein, pharmaceutical compositions including the compounds, and methods of use thereof.

22 Claims, No Drawings

(56) References Cited

FOREIGN PATENT DOCUMENTS

| WO | 2017/109724 A1 | 6/2017 | | |
| WO | 2017/112815 | 6/2017 | | |
| WO | WO-2017136727 A2 * | 8/2017 | ............. | A61K 31/55 |
| WO | 2018073193 A1 | 4/2018 | | |
| WO | WO-2018109097 A1 * | 6/2018 | ................ | A61P 1/00 |

OTHER PUBLICATIONS

Cho, Y.S. et al., "Phosphorylation-driven assembly of the RIP1-RIP3 complex regulates programmed necrosis and virus-induced inflammation" Cell 137(6):1112-1123 (Jun. 12, 2009).

de Almagro, M., et al., "Necroptosis: Pathway diversity and characteristics" Semin Cell Dev Biol 39:56-62 (Mar. 1, 2015).

Degterev, A., et al., "Chemical inhibitor of nonapoptotic cell death with therapeutic potential for ischemic brain injury" Nat Chem Biol., 1(2):112-119 (Jul. 1, 2005).

Degterev, A., et al., "Identification of RIP1 kinase as a specific cellular target of necrostatins" Nat Chem Biol 4(5):313-321 (May 1, 2008).

Dermer, G., et al., "Another anniversary for the war on cancer" Nat Biotechnol 12:320 (Mar. 1, 1994).

Feoktistova, M., et al., "cIAPs block Ripoptosome formation, a RIP1/caspase-8 containing intracellular cell death complex differentially regulated by cFLIP isoforms" Mol Cell 43(3):449-463 (Aug. 5, 2011).

Freshney Culture of Animal Cells: A Manual of Basic Technique (Freshney Animal Cell Culture (1987)), New York: Alan R. Liss, Inc.,3-4 (1983).

Hamilton et al., "Potent and selective inhibitors of receptor-interacting protein kinase 1 that lack an aromatic back pocket group" Bioogranic & Medicinal Chemistry Letters 29(12):1497-1501 (2019).

Harris, P., et al., "Discovery of a First-in-Class Receptor Interacting Protein 1 (RIP1) kinase Specific Clinical Candidate (GSK2982772) for the Treatment of Inflammatory Diseases" J Med Chem 60(4):1247-1261 (Feb. 7, 2017).

Harris, P., et al., "Discovery of Small Molecule RIP1 Kinase Inhibitors for the Treatment of Pathologies Associated with Necroptosis" ACS Chem Lett 4(12):1238-1243 (Nov. 4, 2013).

He, S., et al., "Receptor Interacting Protein Kinase-3 Determines Cellular Necrotic Response to TNF-$\alpha$" Cell 137(6):1100-1111 (Jun. 12, 2009).

Kaiser, W., et al., "Toll-like receptor 3-mediated necrosis via TRIF, RIP3, and MLKL" J Biochem 288(43):31268-31279 (Oct. 25, 2013).

Linkermann, A., et al., "Necroptosis" New Engl J Med 370(5):455-465 (Jan. 30, 2014).

Najjar, M., et al., "Structure Guided Design of Potent and Selective Ponatinib-Based Hybrid Inhibitors for RIPK1" Cell Rep 10(11):1850-1860 (Mar. 24, 2015).

Newton, K. et al., "RIPK1 and RIPK3: critical regulators of inflammation and cell death" Trends Cell Biol 25(6):347-353 (Jun. 1, 2015).

Newton, K., et al., "Activity of protein kinase RIPK3 determines whether cells die by necroptosis or apoptosis" Science 343(6177):1357-1360 (Mar. 21, 2014).

O'Donnell, M., et al., "Ubiquitination of RIP1 regulates an NF-kappaB-independent cell-death switch in TNF signaling" Curr Biol 17(5):418-424 (Mar. 6, 2007).

PCT International Search Report and Written Opinion for PCT/EP2017/076385, dated Dec. 7, 2017, 12 pages.

PCT International Search Report and Written Opinion for PCT/EP2017/082851, dated Feb. 20, 2018, 16 pages.

PCT International Search Report and Written Opinion for PCTUS2019/028011, dated Jul. 9, 2019, 13 pages.

PCT International Search Report and Written Opinion for PCT/US2016/040659, dated Sep. 20, 2016, 10 pages.

Rosauer, K.G., et al., "Novel 3,4-Dihydroquinolin-2(1H)-one Inhibitors of Human Glycogen Phosphorylase a" Bioorg Med Chem Lett 13(24):4385-4388 (Dec. 15, 2003).

Sun, L., et al., "Mixed lineage kinase domain-like protein mediates necrosis signaling downstream of RIP3 kinase" Cell 148(1-2):213-227 (Jan. 20, 2012).

Takahashi, N., et al., "Necrostatin-1 analogues: critical issues on the specificty, activity and in vivo use in experimental disease models" Cell Death Dis 3:e437 (Nov. 29, 2012).

Vanden Berghe, T. et al., "Regulated necrosis: the expanding network of non-apoptotic cell death pathways" Nat Rev Mol Cell Bio 15:135-147 (Feb. 1, 2014).

Wang, L., et al., "TNF-alpha induces two distinct caspase-8 activation pathways" Cell 133(4):693-703 (May 16, 2008).

Wikipedia, Spiro compound, https://en.wikipedia.org/wiki/Sprio_compound, Jul. 30, 2018, 8 pages.

Zhao, J., et al., "Mixed lineage kinase domain-like is a key receptor interacting protein 3 downstream component of TNF-induced necrosis" PNAS 109(14):5322-5327 (Apr. 3, 2012).

* cited by examiner

PYRIDINE LACTAM COMPOUNDS AND METHODS OF USE THEREOF

CROSS-REFERENCE TO RELATED APPLICATIONS

This application is a continuation application of International Patent Application No. PCT/US2019/028011, filed Apr. 18, 2019, which claims benefit of priority to U.S. Provisional Application No. 62/660,397, filed Apr. 20, 2018, both contents of which are incorporated herein in their entirety by reference.

FIELD OF THE INVENTION

The invention relates to organic compounds useful for therapy and/or prophylaxis in a mammal, and in particular to inhibitors of RIP1 kinase useful for treating diseases and disorders associated with inflammation, cell death and others.

BACKGROUND OF THE INVENTION

Receptor-interacting protein-1 ("RIP1") kinase is a serine/threonine protein kinase. RIP1 is a regulator of cell signaling that is involved, among other things, in the mediation of programmed cell death pathways, e.g., necroptosis. The best studied form of necroptotic cell death is initiated by TNFα (tumor necrosis factor), but necroptosis can also be induced by other members of the TNFα death ligand family (Fas and TRAIL/Apo2L), interferons, Toll-like receptors (TLRs) signaling and viral infection via the DNA sensor DAI (DNA-dependent activator of interferon regulatory factor) [1-3]. Binding of TNFα to the TNFR1 (TNF receptor 1) prompts TNFR1 trimerization and formation of an intracellular complex, Complex-I. TRADD (TNF receptor associated death domain protein) binds to the intracellular death domain of TNFR1 and recruits the protein kinase RIP1 (receptor-interacting protein 1) through the death domain present in both proteins [4]. Following initial recruitment into TNFR1-associated signaling complex, RIP1 translocates to a secondary cytoplasmatic complex, Complex-II [5-7]. Complex-II is formed by the death domain containing protein FADD (Fas-associated Protein), RIP1, caspase-8 and cFLIP. If caspase-8 is not fully activated or its activity is blocked, the protein kinase RIP3 gets recruited to the complex, forming a necrosome, which will lead to necroptotic cell death initiation [8-10]. Once the necrosome is formed, RIP1 and RIP3 engage in a series of auto and cross phosphorylation events that are essential for necroptotic cell death. Necroptosis can be completely blocked either by the kinase inactivating mutation in any of the two kinases, or chemically by RIP1 kinase inhibitors (necrostatins), or RIP3 kinase inhibitors [11-13]. Phosphorylation of RIP3 allows the binding and phosphorylation of pseudokinase MLKL (mixed lineage kinase domain-like), a key component of necroptotic cell death [14, 15].

Necroptosis has crucial pathophysiological relevance in myocardial infarction, stroke, atherosclerosis, ischemia-reperfusion injury, inflammatory bowel diseases, retinal degeneration and a number of other common clinical disorders [16]. Therefore, selective inhibitors of RIP1 kinase activity are therefore desired as a potential treatment of diseases mediated by this pathway and associated with inflammation and/or necroptotic cell death.

Inhibitors of RIP1 kinase have been previously described. The first published inhibitor of RIP1 kinase activity was necrostatin 1 (Nec-1) [17]. This initial discovery was followed by modified versions of Nec-1 with various abilities to block RIP1 kinase activity [11, 18]. Recently, additional RIP1 kinase inhibitors have been described that differ structurally from necrostatin class of compounds [19, 20, 21].

References cited above, each of which is hereby incorporated by reference in its entirety:
1) Vanden Berghe, T., Linkermann, A., Jouan-Lanhouet, S., Walczak, H. and Vandenabeele, P. (2014) Regulated necrosis: the expanding network of non-apoptotic cell death pathways. Nature reviews. Molecular cell biology. 15, 135-147.
2) Newton, K. (2015) RIPK1 and RIPK3: critical regulators of inflammation and cell death. Trends in cell biology. 25, 347-353.
3) de Almagro, M. C. and Vucic, D. (2015) Necroptosis: Pathway diversity and characteristics. Semin Cell Dev Biol. 39, 56-62.
4) Chen, Z. J. (2012) Ubiquitination in signaling to and activation of IKK. Immunological reviews. 246, 95-106.
5) O'Donnell, M. A., Legarda-Addison, D., Skountzos, P., Yeh, W. C. and Ting, A. T. (2007) Ubiquitination of RIP1 regulates an NF-kappaB-independent cell-death switch in TNF signaling. Curr Biol. 17, 418-424.
6) Feoktistova, M., Geserick, P., Kellert, B., Dimitrova, D. P., Langlais, C., Hupe, M., Cain, K., MacFarlane, M., Hacker, G. and Leverkus, M. (2011) cIAPs block Ripoptosome formation, a RIP1/caspase-8 containing intracellular cell death complex differentially regulated by cFLIP isoforms. Molecular cell. 43, 449-463.
7) Bertrand, M. J., Milutinovic, S., Dickson, K. M., Ho, W. C., Boudreault, A., Durkin, J., Gillard, J. W., Jaquith, J. B., Morris, S. J. and Barker, P. A. (2008) cIAP1 and cIAP2 facilitate cancer cell survival by functioning as E3 ligases that promote RIP1 ubiquitination. Mol Cell. 30, 689-700.
8) Wang, L., Du, F. and Wang, X. (2008) TNF-alpha induces two distinct caspase-8 activation pathways. Cell. 133, 693-703.
9) He, S., Wang, L., Miao, L., Wang, T., Du, F., Zhao, L. and Wang, X. (2009) Receptor interacting protein kinase-3 determines cellular necrotic response to TNF-alpha. Cell. 137, 1100-1111.
10) Cho, Y. S., Challa, S., Moquin, D., Genga, R., Ray, T. D., Guildford, M. and Chan, F. K. (2009) Phosphorylation-driven assembly of the RIP1-RIP3 complex regulates programmed necrosis and virus-induced inflammation. Cell. 137, 1112-1123.
11) Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem Biol. 4, 313-321.
12) Newton, K., Dugger, D. L., Wickliffe, K. E., Kapoor, N., de Almagro, M. C., Vucic, D., Komuves, L., Ferrando, R. E., French, D. M., Webster, J., Roose-Girma, M., Warming, S. and Dixit, V. M. (2014) Activity of protein kinase RIPK3 determines whether cells die by necroptosis or apoptosis. Science. 343, 1357-1360.
13) Kaiser, W. J., Sridharan, H., Huang, C., Mandal, P., Upton, J. W., Gough, P. J., Sehon, C. A., Marquis, R. W., Bertin, J. and Mocarski, E. S. (2013) Toll-like receptor 3-mediated necrosis via TRIF, RIP3, and MLKL. The Journal of biological chemistry. 288, 31268-31279.
14) Zhao, J., Jitkaew, S., Cai, Z., Choksi, S., Li, Q., Luo, J. and Liu, Z. G. (2012) Mixed lineage kinase domain-like is a key receptor interacting protein 3 downstream component of TNF-induced necrosis. Proceedings of the National Academy of Sciences of the United States of America. 109, 5322-5327.
15) Sun, L., Wang, H., Wang, Z., He, S., Chen, S., Liao, D., Wang, L., Yan, J., Liu, W., Lei, X. and Wang, X. (2012) Mixed Lineage Kinase Domain-like Protein Mediates Necrosis Signaling Downstream of RIP3 Kinase. Cell. 148, 213-227.
16) Linkermann, A. and Green, D. R. (2014) Necroptosis. The New England journal of medicine. 370, 455-465.
17) Degterev, A., Huang, Z., Boyce, M., Li, Y., Jagtap, P., Mizushima, N., Cuny, G. D., Mitchison, T. J., Moskowitz, M. A. and Yuan, J. (2005) Chemical inhibitor of nonapoptotic cell death with therapeutic potential for ischemic brain injury. Nat Chem Biol. 1, 112-119.
18) Takahashi, N., Duprez, L., Grootjans, S., Cauwels, A., Nerinckx, W., DuHadaway, J. B., Goossens, V., Roelandt, R., Van Hauwermeiren, F., Libert, C., Declercq, W., Callewaert, N., Prendergast, G. C., Degterev, A., Yuan, J. and Vandenabeele, P. (2012) Necrostatin-1 analogues: critical issues on the specificity, activity and in vivo use in experimental disease models. Cell Death Dis. 3, e437.
19) Harris, P. A., Bandyopadhyay, D., Berger, S. B., Campobasso, N., Capriotti, C. A., Cox, J. A., Dare, L., Finger, J. N., Hoffman, S. J., Kahler, K. M., Lehr, R., Lich, J. D., Nagilla, R., Nolte, R. T., Ouellette, M. T., Pao, C. S., Schaeffer, M. C., Smallwood, A., Sun, H. H., Swift, B. A., Totoritis, R. D., Ward, P., Marquis, R. W., Bertin, J. and Gough, P. J. (2013) Discovery of Small Molecule RIP1 Kinase Inhibitors for the Treatment of Pathologies Associated with Necroptosis. ACS medicinal chemistry letters. 4, 1238-1243.
20) Najjar, M., Suebsuwong, C., Ray, S. S., Thapa, R. J., Maki, J. L., Nogusa, S., Shah, S., Saleh, D., Gough, P. J., Bertin, J., Yuan, J., Balachandran, S., Cuny, G. D. and Degterev, A. (2015) Structure Guided Design of Potent and Selective Ponatinib-Based Hybrid Inhibitors for RIPK1. Cell Rep.
21) International Patent Publication No. WO 2014/125444.
22) International Patent Publication No. WO 2017/004500.

SUMMARY OF THE INVENTION

Provided herein are compounds of formula I:

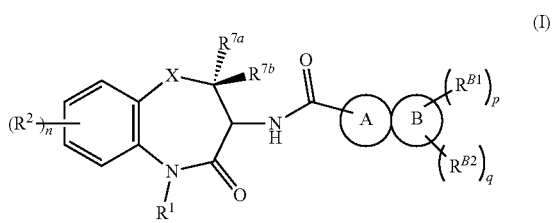

(I)

or pharmaceutically acceptable salts thereof, wherein
$R^1$ is selected from the group consisting of hydrogen, $C_1$-$C_4$ alkyl, and $CD_3$;
each $R^2$ is independently selected from the group consisting of hydrogen, deutero, halogen, cyano, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), $CH_2CH_2$—($C_3$-$C_6$ cycloalkyl), $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2$—($C_5$-$C_6$ heteroaryl), and $CH_2CH_2$—($C_5$-$C_6$ heteroaryl);

n is the integer 0, 1 or 2;
X is selected from the group consisting of O, S, S(O), $SO_2$, $CH_2$, $C(CH_3)_2$, $CF_2$ and $CHCF_3$;
Y is N or C;
the A ring and the B ring are fused to form a polycyclic ring system, wherein
the A ring is either:
(i) a 5 membered heteroaromatic ring having as its only heteroatoms, either (a) two or three nitrogen atoms, (b) one nitrogen atom and one oxygen atom, or (c) one nitrogen atom and one sulfur atom; or
(ii) a 6 membered heteroaromatic ring having as its only heteroatoms 1 to 3 nitrogen atoms;
wherein the A ring is optionally substituted at a carbon atom by one substituent selected from the group consisting of fluoro, chloro, methyl, and trifluoromethyl; and
the B ring is a 5 to 7 membered carbocyclic ring, a 5 to 7 membered heterocyclic ring, or a 5 to 6 membered heteroaryl ring, wherein the heterocyclic or heteroaryl ring has 1 to 3 heteroatoms selected from the group consisting of nitrogen, oxygen, and sulfur;
p is 1 or 2, and q is 0 or 1; or p is 0, and q is 1;
each $R^{B1}$ is independently selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^N$)$_2$, and cyano; wherein two $C_1$-$C_6$ alkyl substituents may together form a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;
$R^{B2}$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^N$)$_2$, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when $R^{B2}$ is phenyl or benzyl the phenyl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;
$R^{7a}$ and $R^{7b}$ are each independently selected from the group consisting of H, halogen, and $C_1$-$C_6$ alkyl; or $R^{7a}$ and $R^{7b}$ may together with the carbon atom to which they are both attached form cyclopropyl; and
each $R^N$ is independently selected from the group consisting of $C_1$-$C_6$ alkyl, $C_3$-$C_6$ cycloalkyl, $C_1$-$C_6$ alkoxy, and $C_1$-$C_6$ haloalkyl; or two $R^N$ together with the nitrogen atom to which they are both attached form a 4-6 membered heterocyclic ring;
provided that if n is 2, only one $R^2$ may be phenyl, benzyl, $CH_2$—($C_3$-$C_6$ cycloalkyl), $CH_2CH_2$—($C_3$-$C_6$ cycloalkyl), $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2$—($C_5$-$C_6$ heteroaryl), or $CH_2CH_2$—($C_5$-$C_6$ heteroaryl).

Also provided herein are pharmaceutical compositions comprising a compound of formula I, or a pharmaceutically acceptable salt thereof, and one or more pharmaceutically acceptable carriers or excipients. Specific embodiments include pharmaceutical compositions suitable for oral delivery.

Also provided herein are oral formulations of a compound of formula I, or a pharmaceutically acceptable salt thereof, and one or more pharmaceutically acceptable carriers or excipients suitable for oral delivery.

Also provided herein are methods of treatment of diseases and disorders associated with inflammation, cell death, and others related to RIP1 kinase, as described further below.

DETAILED DESCRIPTION OF THE INVENTION

Definitions

As provided herein, all chemical formulae and generic chemical structures should be interpreted to provide proper valence and chemically stable bonds between atoms as understood by one of ordinary skill in the art. Where appropriate, substituents may be bonded to more than one adjacent atom (e.g., alkyl includes methylene where two bonds are present).

In the chemical formulae provided herein, "halogen" or "halo" refers to flurorine, chlorine, and bromine (i.e., F, Cl, Br).

Alkyl, unless otherwise specifically defined, refers to an optionally substituted, straight-chain or branched $C_1$-$C_{12}$ alkyl group. In some embodiments, alkyl refers to a $C_1$-$C_6$ alkyl group. Exemplary alkyl groups include methyl, ethyl, propyl, iso-propyl, n-butyl, iso-butyl, tert-butyl, sec-butyl, n-pentyl, n-hexyl, n-heptyl, and n-oxtyl. Substituted alkyl groups provided herein are substituted by one or more substituents selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, the substituted alkyl group has 1 or 2 substituents. In some embodiments, the alkyl group is unsubstituted.

Cycloalkyl, unless otherwise specifically defined, refers to an optionally substituted $C_3$-$C_{12}$ cycloalkyl group and includes fused, spirocyclic, and bridged bicyclic groups, wherein the substituents are selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, cycloalkyl refers to a $C_3$-$C_6$ cycloalkyl group. In some embodiments, the $C_3$-$C_6$ cycloalkyl group is optionally substituted with 1 to three halogen atoms. In some embodiments, the $C_3$-$C_6$ cycloalkyl group is optionally substituted with 1 to three fluorine atoms. Exemplary $C_3$-$C_6$ cycloalkyl groups include cyclopropyl, cyclobutyl, cyclopentyl and cyclohexyl. Exemplary $C_3$-$C_{12}$ cycloalkyl groups further include bicyclo[3.1.0]hexyl, bicyclo[2.1.1]hexyl, cycloheptyl, bicycle[4.1.0]heptyl, spiro[4.2]heptyl, cyclooctyl, spiro[4.3]octyl, spiro[5.2]octyl, bicyclo[2.2.1]heptanyl, bicycle[2.2.2]octanyl, adamantanyl, decalinyl, and spiro[5.4]decanyl. Where appropriate, cycloalkyl groups may be fused to other groups such that more than one chemical bond exists between the cycloalkyl group and another ring system (e.g., the C ring of formula I). In some embodiments, the cycloalkyl group is unsubstituted.

Haloalkyl, unless otherwise specifically defined, refers to a straight-chain or branched $C_1$-$C_{12}$ alkyl group, wherein one or more hydrogen atoms are replaced by a halogen. In some embodiments, haloalkyl refers to a $C_1$-$C_6$ haloalkyl group. In some embodiments, 1 to 3 hydrogen atoms of the haloalkyl group are replaced by a halogen. In some embodiments, every hydrogen atom of the haloalkyl group is replaced by a halogen (e.g., trifluoromethyl). In some embodiments, the haloalkyl is as defined herein wherein the halogen in each instance is fluorine. Exemplary haloalkyl groups include fluoromethyl, difluoromethyl, trifluromethyl, trifluoroethyl, and pentafluoroethyl.

Alkoxy, unless otherwise specifically defined, refers to a straight-chain or branched $C_1$-$C_{12}$ alkyl group, wherein one or more oxygen atoms are present, in each instance between two carbon atoms. In some embodiments, alkoxy refers to a $C_1$-$C_6$ alkoxy group. In some embodiments, $C_1$-$C_6$ alkoxy groups provided herein have one oxygen atom. Exemplary alkoxy groups include methoxy, ethoxy, $CH_2OCH_3$, $CH_2CH_2OCH_3$, $CH_2OCH_2CH_3$, $CH_2CH_2OCH_2CH_3$, $CH_2OCH_2CH_2CH_3$, $CH_2CH_2CH_2OCH_3$, $CH_2OCH(CH_3)_2$, $CH_2OC(CH_3)_3$, $CH(CH_3)OCH_3$, $CH_2CH(CH_3)OCH_3$, $CH(CH_3)OCH_2CH_3$, $CH_2OCH_2OCH_3$, $CH_2CH_2OCH_2CH_2OCH_3$, and $CH_2OCH_2OCH_2OCH_3$.

Cycloalkoxy, unless otherwise specifically defined, refers to a $C_4$-$C_{10}$ or a $C_4$-$C_6$ alkoxy group as defined above wherein the group is cyclic and contains one oxygen atom. Exemplary cycloalkoxy groups include oxetanyl, tetrahydrofuranyl, and tetrahydropyranyl.

Haloalkoxy, unless otherwise specifically defined, refers to a $C_1$-$C_6$ haloalkyl group as defined above, wherein one or two oxygen atoms are present, in each instance between two carbon atoms. In some embodiments, $C_1$-$C_6$ haloalkoxy groups provided herein have one oxygen atom. Exemplary haloalkoxy groups include $OCF_3$, $OCHF_2$ and $CH_2OCF_3$.

Thioalkyl, unless otherwise specifically defined, refers to a $C_1$-$C_6$ alkoxy group as defined above wherein the oxygen atom is replaced by a sulfur atom. In some embodiments, thioalkyl groups may include sulfur atoms substituted by one or two oxygen atoms (i.e., alkylsulfones and alkylsulfoxides). Exemplary thioalkyl groups are those exemplified in the definition of alkoxy above, wherein each oxygen atom is replaced by a sulfur atom in each instance.

Alkoxycarbonyl, unless otherwise specifically defined, refers to a $C_1$-$C_6$ alkoxy group as defined above wherein the oxygen atom is bonded to a carbonyl group to form an ester. Exemplary alkoxycarbonyl groups include $CH_3OC(O)$— and $CH_3CH_2OC(O)$—.

Cyanoalkyl, unless otherwise specifically defined, refers to a $C_1$-$C_6$ alkyl group as defined above wherein one hydrogen atom is replaced by a cyano group ("—CN"). Exemplary cyanoalkyl groups include $CNCH_2$— and $CNCH_2CH_2$—.

Alkylsulfonyl, unless otherwise specifically defined, refers to a $C_1$-$C_6$ alkyl group as defined above wherein a carbon atom is bonded to a sulfone group ("$SO_2$"), which is in turn bound to a $C_1$-$C_6$ alkyene. Exemplary alkylsulfonyl groups include $CH_3SO_2CH_2$— and $CH_3SO_2CH_2CH_2$—.

Heterocyclyl, unless otherwise specifically defined, refers to a single saturated or partially unsaturated 4 to 8 membered ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems have from 7 to 12 atoms and are further described below. Thus, the term includes single saturated or partially unsaturated rings (e.g., 3, 4, 5, 6, 7 or 8 membered rings) from about 1 to 7 carbon atoms and from about 1 to 4 heteroatoms selected from the group consisting of oxygen, nitrogen and sulfur in the ring. The ring may be C-branched (i.e., substituted by $C_1$-$C_4$ alkyl). The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The rings of the multiple condensed ring system can be connected to each other via fused, Spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system. It is also to be understood that the point of attachment for a heterocycle or heterocycle multiple condensed ring system can be at any suitable atom of the heterocyclyl group including a carbon atom and a nitrogen atom. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo [2.2.2]octane and pyrrolidin-2-one.

In some embodiments, the heterocyclyl is a $C_4$-$C_{10}$ heterocyclyl having 1 to 3 heteroatoms selected from the group consisting of nitrogen, oxygen and sulfur. In some embodiments, the heterocyclyl group is neither bicyclic nor spirocyclic. In some embodiments, the heterocyclyl is a $C_5$-$C_6$ heterocyclyl having 1 to 3 heteroatoms, wherein at least 2 are nitrogen if 3 heteroatoms are present.

Aryl, unless otherwise specifically defined, refers to a single all carbon aromatic ring or a multiple condensed all carbon ring system wherein at least one of the rings is aromatic and wherein the aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Exemplary aryl groups include phenyl, indenyl, naphthyl, 1, 2, 3, 4-tetrahydronaphthyl, anthracenyl, and the like.

Heteroaryl, unless otherwise specifically defined, refers to a 5 to 6 membered aromatic ring that has at least one atom other than carbon in the ring, wherein the atom is selected from the group consisting of oxygen, nitrogen and sulfur; "heteroaryl" also includes multiple condensed ring systems having 8 to 16 atoms that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2 or 3 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1 to 15 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "~~~" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see P.G.M. Wuts and T.W. Greene, Greene's Protective Groups in Organic Synthesis 4th edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6}$)alkyl$)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds;

the racemates, diastereomers, geometric isomers, regioisomers and individual isomers (e.g., separate enantiomers) are all intended to be encompassed within the scope of the present invention.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Inhibitors of RIP1 Kinase

The present invention provides novel compounds having the general formula I:

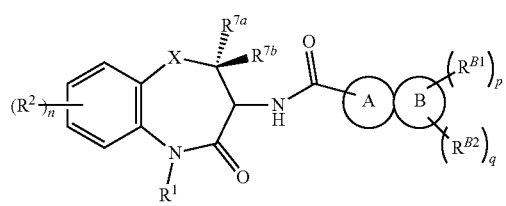

or pharmaceutically acceptable salts thereof, wherein
$R^1$ is selected from the group consisting of hydrogen, $C_1$-$C_4$ alkyl, and $CD_3$;

each $R^2$ is independently selected from the group consisting of hydrogen, deutero, halogen, cyano, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_3$-$C_6$ cycloalkyl), $CH_2CH_2$—($C_3$-$C_6$ cycloalkyl), $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2$—($C_5$-$C_6$ heteroaryl), and $CH_2CH_2$—($C_5$-$C_6$ heteroaryl);

n is 0, 1 or 2;

X is selected from the group consisting of O, S, S(O), $SO_2$, $CH_2$, $CH(CH_3)$, $C(CH_3)_2$, $CF_2$ and $CHCF_3$;

Y is N or C;

the A ring and the B ring are fused to form a polycyclic ring system, wherein the A ring is either:

(i) a 5 membered heteroaromatic ring having as its only heteroatoms, either (a) two or three nitrogen atoms, (b) one nitrogen atom and one oxygen atom, or (c) one nitrogen atom and one sulfur atom; or (ii) a 6 membered heteroaromatic ring having as its only heteroatoms 1 to 3 nitrogen atoms;

wherein the A ring is optionally substituted at a carbon atom by one substituent selected from the group consisting of fluoro, chloro, methyl, and trifluoromethyl; and the B ring is a 5 to 7 membered carbocyclic ring, a 5 to 7 membered heterocyclic ring, or a 5 to 6 membered heteroaryl ring, wherein the heterocyclic or heteroaryl ring has 1 to 3 heteroatoms selected from the group consisting of nitrogen, oxygen, and sulfur;

p is 1 or 2, and q is 0 or 1; or p is 0, and q is 1;

each $R^{B1}$ is independently selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, and cyano; wherein two $C_1$-$C_6$ alkyl substituents may together form a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;

$R^{B2}$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when $R^{B2}$ is phenyl or benzyl the phenyl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;

$R^{7a}$ and $R^{7b}$ are each independently selected from the group consisting of H, halogen, and $C_1$-$C_6$ alkyl; or $R^{7a}$ and $R^{7b}$ may together with the carbon atom to which they are both attached form cyclopropyl; and each $R^N$ is independently selected from the group consisting of $C_1$-$C_6$ alkyl, $C_3$-$C_6$ cycloalkyl, $C_1$-$C_6$ alkoxy, and $C_1$-$C_6$ haloalkyl; or two $R^N$ together with the nitrogen atom to which they are both attached form a 4-6 membered heterocyclic ring;

provided that if n is 2, only one $R^2$ may be phenyl, benzyl, $CH_2$—($C_3$-$C_6$ cycloalkyl), $CH_2CH_2$—($C_3$-$C_6$ cycloalkyl), $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2$—($C_5$-$C_6$ heteroaryl), or $CH_2CH_2$—($C_5$-$C_6$ heteroaryl).

In certain embodiments the compounds are of formula (Ia):

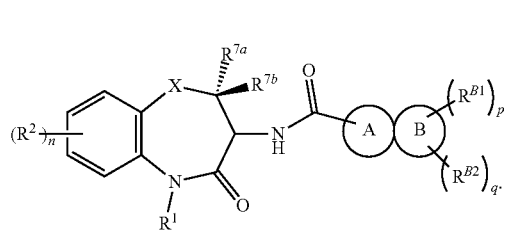

(Ia)

In some embodiments of formula (I) or formula (Ia), X is O or $CH_2$. In some embodiments, X is O. In some embodiments, X is $CH_2$.

In some embodiments of formula (I) or formula (Ia), $R^1$ is selected from the group consisting of hydrogen, methyl, and $CD_3$. In some embodiments $R^1$ is methyl. In some embodiments $R^1$ is $CD_3$.

In some embodiments of formula (I) or formula (Ia), each $R^2$ is independently selected from the group consisting of hydrogen, deutero, halogen, cyano, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, and benzyl.

In some embodiments of formula (I) or formula (Ia), each $R^2$ is independently selected from the group consisting of hydrogen, deutero, halogen, cyano, $C_1$-$C_6$ alkyl, $C_1$-$C_6$ haloalkyl, $C_3$-$C_6$ cycloalkyl, $C_1$-$C_6$ alkoxy, and $C_1$-$C_6$ haloalkoxy. In some embodiments, each $R^2$ is independently selected from the group consisting of hydrogen, halogen, $C_1$-$C_4$ alkyl, and $C_1$-$C_4$ haloalkyl.

In some embodiments of formula (I) or formula (Ia), the A ring and the B ring together (including substituents, p, q, $R^{B1}$ and $R^{B2}$) are selected from the group consisting of:

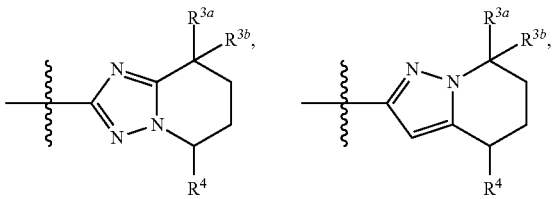

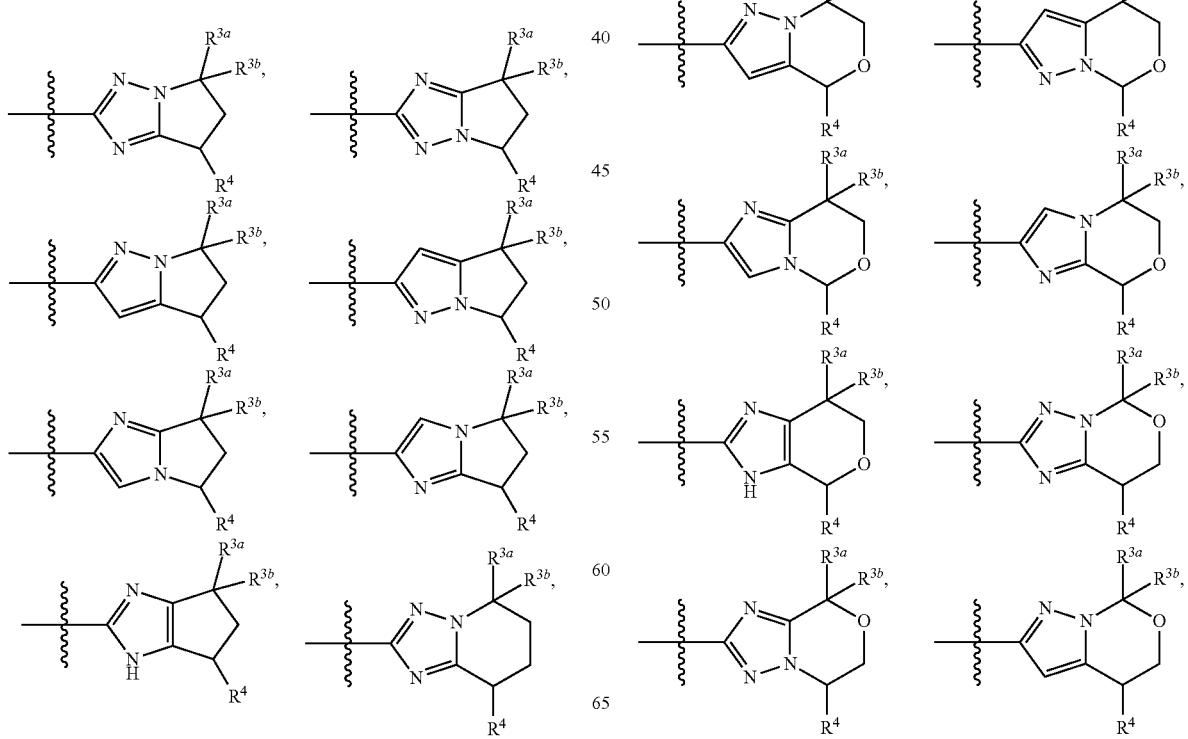

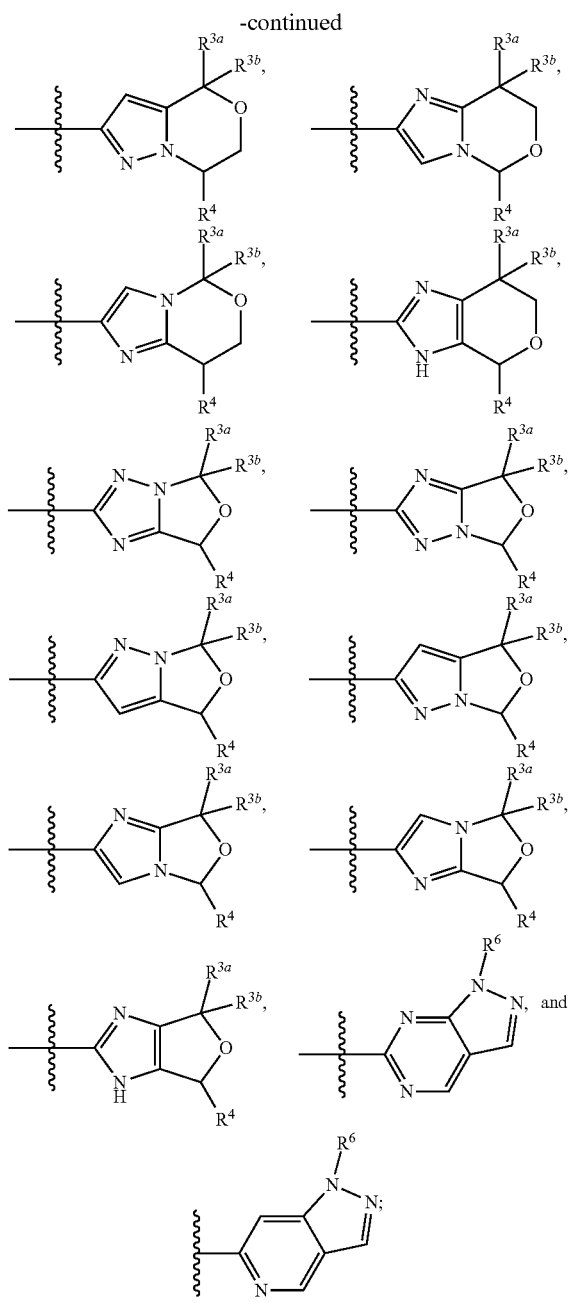

wherein
R$^{3a}$ and R$^{3b}$ are selected as follows:
(i) one of R$^{3a}$ and R$^{3b}$ is H, and the other is selected from the group consisting of H, D, F, Cl, OH, CN, C$_1$-C$_4$ alkyl, C$_1$-C$_4$ haloalkyl, cyclopropyl, C$_1$-C$_4$ alkoxy and C$_1$-C$_4$ haloalkoxy;
(ii) each of R$^{3a}$ and R$^{3b}$ is independently selected from the group consisting of D, F, Cl, OH, CN and methyl, provided that R$^{3a}$ and R$^{3b}$ cannot both be OH or CN; or
(iii) R$^{3a}$ and R$^{3b}$, together with the adjacent carbon atom, form cyclopropyl;
R$^4$ is selected from the group consisting of C$_1$-C$_6$ alkyl, C$_1$-C$_6$ haloalkyl, C$_3$-C$_6$ cycloalkyl, C$_1$-C$_6$ alkoxy, C$_1$-C$_6$ haloalkoxy, C$_1$-C$_6$ thioalkyl, phenyl, benzyl, CH$_2$—(C$_3$-C$_6$ cycloalkyl), CH$_2$CH$_2$—(C$_3$-C$_6$ cycloalkyl), CH$_2$-(4 to 6 membered heterocyclyl), CH$_2$CH$_2$-(4 to 6 membered heterocyclyl), 5 to 6 membered heteroaryl, and CH$_2$-(5 to 6 membered heteroaryl); wherein when a phenyl ring is present it may be substituted by 1 to 3 substituents selected from the group consisting of halogen, C$_1$-C$_4$ alkyl, C$_1$-C$_4$ haloalkyl, C$_1$-C$_4$ alkoxy, C$_1$-C$_4$ haloalkoxy, and cyano; and
R$^6$ is selected from the group consisting of H, C$_1$-C$_6$ alkyl, C$_1$-C$_6$ haloalkyl, and C$_3$-C$_6$ cycloalkyl.

In some embodiments of formula (I), the A ring and the B ring together are

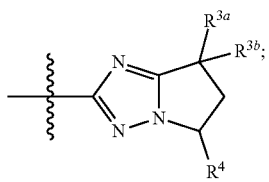

wherein
R$^{3a}$ and R$^{3b}$ are selected as follows:
(i) one of R$^{3a}$ and R$^{3b}$ is H, and the other is selected from the group consisting of H, D, F, Cl, OH, CN, C$_1$-C$_4$ alkyl, C$_1$-C$_4$ haloalkyl, cyclopropyl, C$_1$-C$_4$ alkoxy and C$_1$-C$_4$ haloalkoxy;
(ii) each of R$^{3a}$ and R$^{3b}$ is independently selected from the group consisting of D, F, Cl, OH, CN and methyl, provided that R$^{3a}$ and R$^{3b}$ cannot both be OH or CN; or
(iii) R$^{3a}$ and R$^{3b}$, together with the adjacent carbon atom, form cyclopropyl;
R$^4$ is selected from the group consisting of C$_1$-C$_6$ alkyl, C$_1$-C$_6$ haloalkyl, C$_3$-C$_6$ cycloalkyl, C$_1$-C$_6$ alkoxy, C$_1$-C$_6$ haloalkoxy, C$_1$-C$_6$ thioalkyl, phenyl, benzyl, CH$_2$—(C$_3$-C$_6$ cycloalkyl), CH$_2$CH$_2$—(C$_3$-C$_6$ cycloalkyl), CH$_2$-(4 to 6 membered heterocyclyl), CH$_2$CH$_2$-(4 to 6 membered heterocyclyl), 5 to 6 membered heteroaryl, and CH$_2$-(5 to 6 membered heteroaryl); wherein when a phenyl ring is present it may be substituted by 1 to 3 substituents selected from the group consisting of halogen, C$_1$-C$_4$ alkyl, C$_1$-C$_4$ haloalkyl, C$_1$-C$_4$ alkoxy, C$_1$-C$_4$ haloalkoxy, and cyano.

In some embodiments of formula (I) or formula (Ia), the A ring and the B ring together are

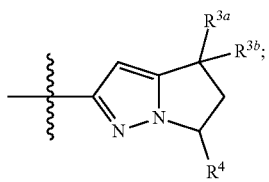

wherein R$^{3a}$, R$^{3b}$ and R$^4$ are as defined herein.

In some embodiments of formula (I) or formula (Ia), the A ring and the B ring together are

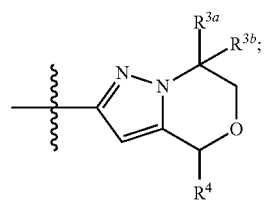

wherein R$^{3a}$, R$^{3b}$ and R$^4$ are as defined herein.

In some embodiments of formula (I) or formula (Ia), the A ring and the B ring together are selected from the group consisting of:

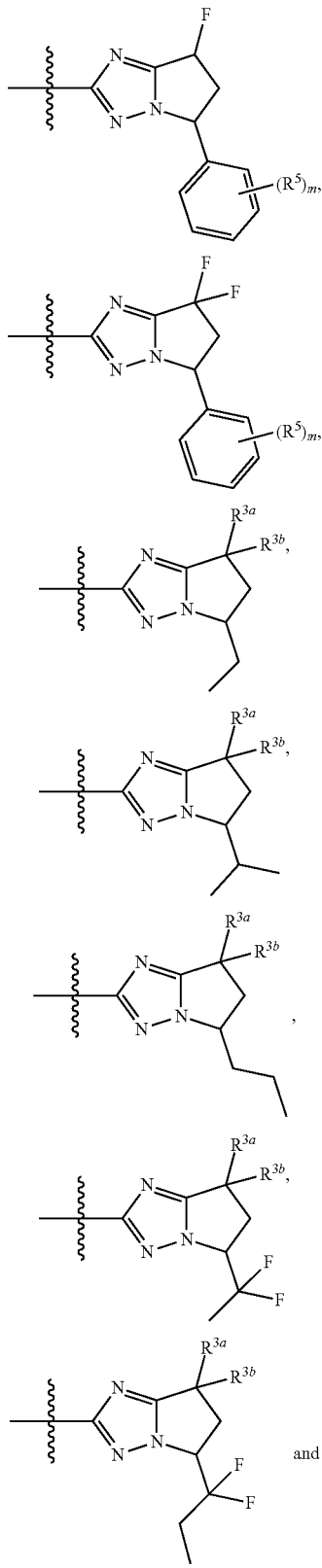

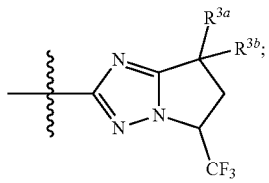

wherein $R^{3a}$ and $R^{3b}$ are selected as follows:

(i) one of $R^{3a}$ and $R^{3b}$ is H, and the other is selected from the group consisting of H, D, F, Cl, OH, CN, $C_1$-$C_4$ alkyl, $C_1$-$C_4$ haloalkyl, cyclopropyl, $C_1$-$C_4$ alkoxy and $C_1$-$C_4$ haloalkoxy;

(ii) each of $R^{3a}$ and $R^{3b}$ is independently selected from the group consisting of D, F, Cl, OH, CN and methyl, provided that $R^{3a}$ and $R^{3b}$ cannot both be OH or CN; or (iii) $R^{3a}$ and $R^{3b}$ together form cyclopropyl;

each $R^5$ is independently selected from the group consisting of H, F, Cl, $C_1$-$C_6$ alkyl, $C_1$-$C_6$ haloalkyl, $C_1$-$C_6$ alkoxy and $C_1$-$C_6$ haloalkoxy; and m is 1, 2 or 3.

In some embodiments of formula (I) or formula (Ia), the A ring and the B ring together are:

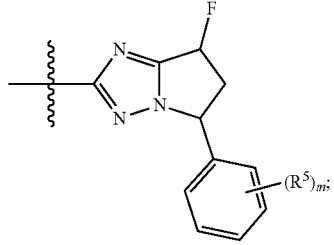

wherein each $R^5$ is selected from the group consisting of H, F, Cl, $C_1$-$C_6$ alkyl, $C_1$-$C_6$ haloalkyl, $C_1$-$C_6$ alkoxy and $C_1$-$C_6$ haloalkoxy; and m is 1, 2 or 3.

In some embodiments of formula (I) or formula (Ia), the A ring and the B ring together are

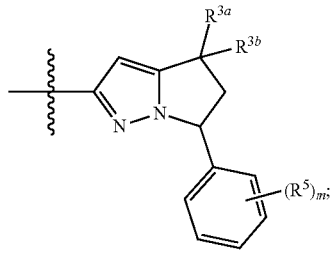

wherein $R^{3a}$, $R^{3b}$ and $R^4$ are as defined herein.

In some embodiments of formula (I) or formula (Ia), the A ring and the B ring together are

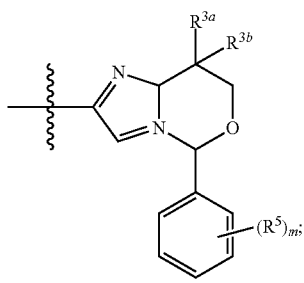

wherein $R^{3a}$, $R^{3b}$ and $R^4$ are as defined herein.

In some embodiments of formula (I) or formula (Ia), the A ring and the B ring together are selected from the group consisting of:

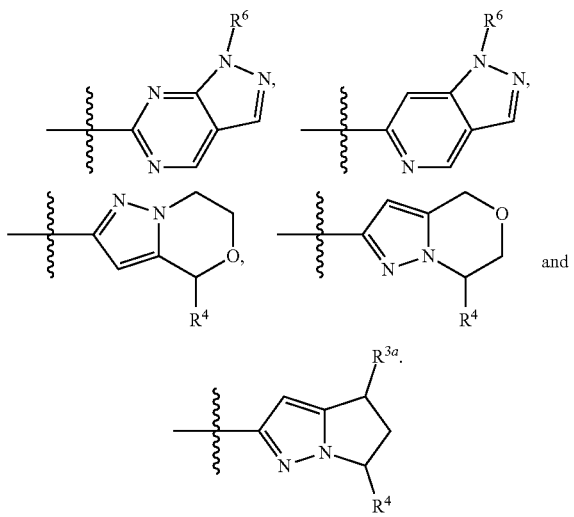

In some embodiments of formula (I) or formula (Ia), the A ring and the B ring together are selected from the group consisting of:

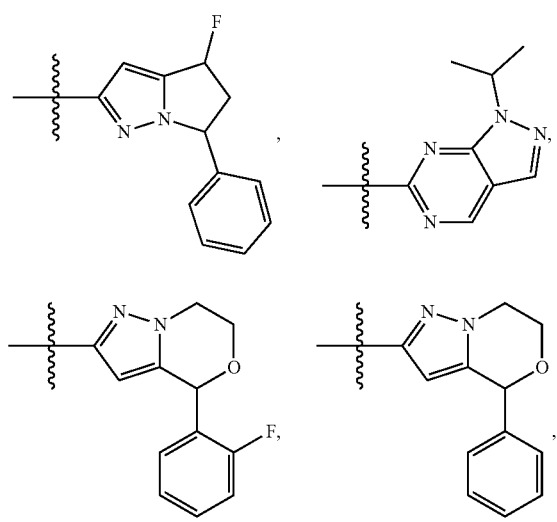

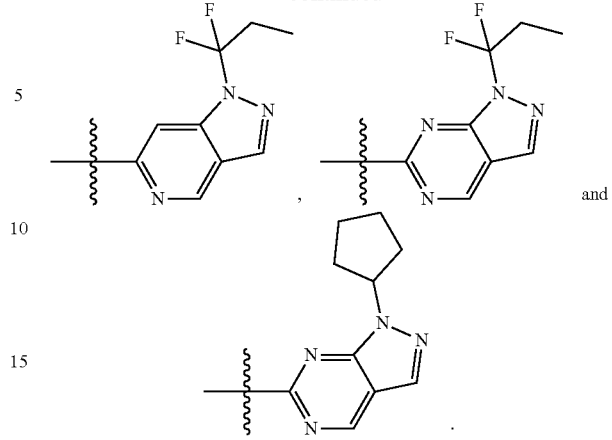

In some of the above embodiments, $R^{3a}$ and $R^{3b}$ are each H. In some of the above embodiments, $R^{3a}$ is H and $R^{3b}$ is D. In some of the above embodiments, $R^{3a}$ is H and $R^{3b}$ is F. In some of the above embodiments, $R^{3a}$ is H and $R^{3b}$ is Cl. In some of the above embodiments, $R^{3a}$ and $R^{3b}$ are each D. In some of the above embodiments, $R^{3a}$ and $R^{3b}$ are each F. In some of the above embodiments, $R^{3a}$ and $R^{3b}$ are each Cl. In some of the above embodiments, $R^{3a}$ and $R^{3b}$ are each methyl. In some of the above embodiments, $R^{3a}$ is methyl and $R^{3b}$ is F. In some of the above embodiments, $R^{3a}$ is methyl and $R^{3b}$ is Cl. In some of the above embodiments, $R^{3a}$ is methyl and $R^{3b}$ is OH. In some of the above embodiments, $R^{3a}$ is methyl and $R^{3b}$ is CN.

In some of the above embodiments, $R^4$ is phenyl. In some embodiments, $R^4$ is mono- or difluorophenyl. In some embodiments, $R^4$ is monofluorophenyl. In some embodiments, $R^4$ is mono- or dichlorophenyl. In some embodiments, $R^4$ is monochlorophenyl.

In some of the above embodiments, $R^5$ is selected from the group consisting of H, F, Cl, $CH_3$, $CH_2CH_3$, $OCH_3$, $CF_3$, $OCF_3$, $CF_2H$, and $OCF_2H$. In some of the above embodiments, $R^5$ is H. In some of the above embodiments, $R^5$ is F. In some of the above embodiments, $R^5$ is Cl. In some of the above embodiments, $R^5$ is $CH_3$. In some of the above embodiments, $R^5$ is $CF_3$.

In some of the above embodiments, $R^6$ is selected from the group consisting of $C_1$-$C_6$ alkyl, $C_1$-$C_6$ haloalkyl and $C_3$-$C_6$ cycloalkyl. In some of the above embodiments, $R^6$ is $C_1$-$C_6$ alkyl. In some of the above embodiments, $R^6$ is $C_1$-$C_6$ haloalkyl. In some of the above embodiments, $R^6$ is $C_3$-$C_6$ cycloalkyl.

In some of the above embodiments, $R^{7a}$ and $R^{7b}$ are each independently selected from the group consisting of H, F, Cl, and $C_1$-$C_6$ alkyl; or $R^{7a}$ and $R^{7b}$ may together with the carbon atom to which they are both attached form cyclopropyl. In some embodiments, $R^{7a}$ and $R^{7b}$ are each independently selected from the group consisting of H, F, and $C_1$-$C_6$ alkyl; or $R^{7a}$ and $R^{7b}$ may together with the carbon atom to which they are both attached form cyclopropyl. In some embodiments, $R^{7a}$ and $R^{7b}$ are each independently selected from the group consisting of H and $C_1$-$C_6$ alkyl. In some embodiments, one of $R^{7a}$ and $R^{7b}$ is H and the other is $C_1$-$C_6$ alkyl. In some embodiments, one of $R^{7a}$ and $R^{7b}$ is H and the other is methyl. In some embodiments, one of $R^{7a}$ and $R^{7b}$ is H and the other is F. In some embodiments, one of $R^{7a}$ and $R^{7b}$ is F and the other is methyl. In some embodiments, each of $R^{7a}$ and $R^{7b}$ is H. In some embodiments, each of $R^{7a}$ and $R^{7b}$ is F. In some embodiments, each of $R^{7a}$ and $R^{7b}$ is methyl.

In some of the above embodiments, each $R^N$ is independently selected from the group consisting of H and $C_1$-$C_6$ alkyl. In some embodiments, each $R^N$ is a $C_1$-$C_4$ alkyl. In some embodiments, each $R^N$ is methyl.

In some of the above embodiments, n is 0. In some of the above embodiments, n is 1. In some embodiments, n is 2.

In some of the above embodiments, m is 0. In some embodiments, m is 1. In some embodiments, m is 2.

In some of the above embodiments, X is O, n is 0 and $R^1$ is methyl or $CD_3$. In some embodiments, X is O, n is 0 and $R^1$ is methyl.

Also provided herein is a compound selected from the compounds of Table 1 below or a pharmaceutically acceptable salt thereof. In another embodiment, provided herein is a compound of Table 1 having a $K_i$ of less than 100 nM in a RIP1K biochemical or cell-based assay, including as herein described. In another embodiment, the compound of Table 1 has a $K_i$ of less than 50 nM in a RIP1K biochemical or cell-based assay, including as herein described. In yet another embodiment, the compound of Table 1 has a $K_i$ of less than 25 nM in a RIP1K biochemical or cell-based assay, including as herein described. In yet another embodiment, the compound of Table 1 has a $K_i$ of less than 10 nM in a RIP1K biochemical or cell-based assay, including as herein described.

In some embodiments, provided herein is a single stereoisomer of a compound of Table 1, as characterized by reference to its chiral separation and isolation (e.g., as described in the Examples by chiral SFC).

In some embodiments, provided herein are pharmaceutical compositions comprising a compound of formula I as described in any one of the above embodiments, or a pharmaceutically acceptable salt thereof, and one or more pharmaceutically acceptable carriers or excipients. Specific embodiments include pharmaceutical compositions suitable for oral delivery.

Also provided herein are oral formulations of a compound of formula I as described in any one of the above embodiments, or a pharmaceutically acceptable salt thereof, and one or more pharmaceutically acceptable carriers or excipients suitable for oral delivery.

Also provided herein are parenteral formulations of a compound of formula I, or a pharmaceutically acceptable salt thereof, and one or more pharmaceutically acceptable carriers or excipients suitable for parenenteral delivery.

In some embodiments, provided herein are uses of a compound of formula I, or a pharmaceutically acceptable salt thereof, for the treatment of diseases and disorders. In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, antiphospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury(AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa and retinal degeneration.

In some embodiments, provided herein are uses of a compound of formula I as described in any one of the above embodiments, or a pharmaceutically acceptable salt thereof, for the treatment of neurodegenerative diseases and disorders. In some embodiments, the diseases and disorders to be treated are synucleopathies such as Parkinson's Disease, Lewy body dementia, multiple system atrophy, Parkinson-plus syndromes. In some embodiments, the diseases and disorders to be treated are taupathies such as Alzheimer's Disease and frontotemporal dementia. In some embodiments, the diseases and disorders to be treated are demyelination diseases such as multiple sclerosis.

In some embodiments, the diseases and disorders to be treated are other neurodegenerative diseases such as amyotrophic lateral sclerosis, spinal muscular atrophy, primary lateral sclerosis, Huntington's disease, ischemia, and stroke. Additional exemplary neurodegenerative diseases to be treated as provided herein include, but are not limited to, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

In some embodiments, the disease or disorder to be treated is Alzheimer's disease. In some embodiments, the disease or disorder to be treated is Parkinson's disease. In some embodiments, the disease or disorder to be treated is Huntington's disease. In some embodiments, the disease or disorder to be treated is multiple sclerosis. In some embodiments, the disease or disorder to be treated is amyotrophic lateral sclerosis (ALS). In some embodiments, the disease or disorder to be treated is spinal muscular atrophy (SMA).

In some embodiments, the disease or disorder to be treated is an inflammatory bowel disease. In some embodiments, the disease or disorder to be treated is Crohn's disease. In some embodiments, the disease or disorder to be treated is ulcerative colitis. In some embodiments, the disease or disorder to be treated is glaucoma. In some embodiments, the disease or disorder to be treated is psoriasis. In some embodiments, the disease or disorder to be treated is rheumatoid arthritis. In some embodiments, the disease or disorder to be treated is spondyloarthritis. In some embodiments, the disease or disorder to be treated is juvenile idiopathic arthritis. In some embodiments, the disease or disorder to be treated is osteoarthritis.

In some embodiments, provided herein are methods for the treatment or prevention of a disease or disorder with a therapeutically effective amount of a compound of formula I, or a pharmaceutically acceptable salt thereof, wherein the disease or disorder is associated with inflammation and/or necroptosis. In some embodiments said disease or disorder is selected from the specific diseases and disorders recited herein.

In some embodiments, provided herein are methods of inhibiting RIP1 kinase activity by contacting a cell with a compound of formula I or a pharmaceutically acceptable salt thereof Pharmaceutical Compositions and Administration Provided herein are pharmaceutical compositions or medicaments containing the compounds of the invention (or stereoisomers, geometric isomers, tautomers, solvates, metabolites, isotopes, pharmaceutically acceptable salts, or prodrugs thereof), and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In some embodiments, the "effective amount" of the compound to be administered will be governed by such considerations, and is the minimum amount necessary to inhibit RIP1 kinase activity in order to provide a therapeutic effect in the mammal being treated. In addition, such an effective amount may be below the amount that is toxic to normal cells, or the mammal as a whole.

In one example, the pharmaceutically effective amount of the compound of the invention administered intravenously or parenterally will be in the per dose range of about 0.1 to 100 mg/kg, alternatively about 0.1 to 20 mg/kg of patient body weight per day, or alternatively about 0.3 to 15 mg/kg/day.

In another embodiment, oral unit dosage forms, such as tablets and capsules, preferably contain from about 1 to about 1000 mg (e.g., 1 mg, 5 mg, 10 mg, 15 mg, 20 mg, 25 mg, 30 mg, 40 mg, 50 mg, 100 mg, 200 mg, 250 mg, 400 mg, 500 mg, 600 mg, 700 mg, 800 mg, 900 mg, or 1000 mg) of the compound of the invention. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

In some embodiments, a low dose of the compound of the invention is administered in order to provide therapeutic benefit while minimizing or preventing adverse effects.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In specific embodiments, the compound of formula I is administered orally. In other specific embodiments, the compound of formula I is administered intravenously.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

An example of a suitable oral dosage form provided herein is a tablet containing about 1 to about 500 mg (e.g., about 1 mg, 5 mg, 10 mg, 25 mg, 30 mg, 50 mg, 80 mg, 100 mg, 150 mg, 250 mg, 300 mg and 500 mg) of the compound of the invention compounded with suitable amounts of anhydrous lactose, sodium croscarmellose, polyvinylpyrrolidone (PVP) K30, and magnesium stearate. The powdered ingredients are first mixed together and then mixed with a solution of the PVP. The resulting composition can be dried, granulated, mixed with the magnesium stearate and compressed to tablet form using conventional equipment.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use.

Extemporaneous injection solutions and suspensions are prepared from sterile powders, granules and tablets of the kind previously described.

An embodiment, therefore, includes a pharmaceutical composition comprising a compound of formula I, or pharmaceutically acceptable salt thereof. In a further embodiment includes a pharmaceutical composition comprising a compound of formula I, or a pharmaceutically acceptable salt thereof, together with a pharmaceutically acceptable carrier or excipient.

When the binding target is located in the brain, certain embodiments of the invention provide for a compound of formula I (or an embodiment thereof) to traverse the blood-brain barrier. In these embodiments, the compounds provided herein exhibit sufficient brain penetration as potential therapeutics in neurological diseases. In some embodiments, brain penetration is assessed by evaluating free brain/plasma ratio ($B_u/P_u$) as measured in vivo pharmacokinetic studies in rodents or by other methods known to persons skilled in the art (see, e.g., Liu, X. et al., J. Pharmacol. Exp. Therap., 325:349-56, 2008).

Certain neurological diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods. Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™ Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Publication No. 2002/0025313), and coating a compound of formula I (or an embodiment thereof) in low-density lipoprotein particles (see, e.g., U.S. Patent Publication No. 2004/0204354) or apolipoprotein E (see, e.g., U.S. Patent Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Publication Nos. 2002/0065259, 2003/0162695, and 2005/0124533); activating potassium channels (see, e.g., U.S. Patent Publication No. 2005/0089473), inhibiting ABC drug transporters (see, e.g., U.S. Patent Publication No. 2003/0073713); coating a compound of formula I or I-I (or an embodiment thereof) with a transferrin and modulating activity of the one or more transferrin receptors (see, e.g., U.S. Patent Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

The compounds of the invention inhibit RIP1 kinase activity. Accordingly, the compounds of the invention are useful for the treatment of diseases and disorders mediated by this pathway and associated with inflammation and/or necroptotic cell death.

In some embodiments, the disease or disorder to be treated is a neurodegenerative disease or disorder. In some embodiments, the diseases and disorders to be treated are synucleopathies such as Parkinson's Disease, Lewy body dementia, multiple system atrophy, Parkinson-plus syndromes. In some embodiments, the diseases and disorders to be treated are taupathies such as Alzheimer's Disease and frontotemporal dementia. In some embodiments, the diseases and disorders to be treated are demyelination diseases such as multiple sclerosis.

In some embodiments, the diseases and disorders to be treated are other neurodegenerative diseases such as amyotrophic lateral sclerosis, spinal muscular atrophy, primary lateral sclerosis, Huntington's disease, ischemia, and stroke. Additional exemplary neurodegenerative diseases to be treated as provided herein include, but are not limited to, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

In some embodiments, the disease or disorder to be treated is Alzheimer's disease. In some embodiments, the disease or disorder to be treated is Parkinson's disease. In some embodiments, the disease or disorder to be treated is Huntington's disease. In some embodiments, the disease or disorder to be treated is multiple sclerosis. In some embodiments, the disease or disorder to be treated is amyotrophic lateral sclerosis (ALS). In some embodiments, the disease or disorder to be treated is spinal muscular atrophy (SMA).

In some embodiments, the disease or disorder to be treated is an inflammatory disease or disorder. In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atrophy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the disease or disorder to be treated is an inflammatory bowel disease. In some embodiments, the disease or disorder to be treated is Crohn's disease. In some embodiments, the disease or disorder to be treated is ulcerative colitis. In some embodiments, the disease or disorder to be treated is glaucoma. In some embodiments, the disease or disorder to be treated is psoriasis. In some embodiments, the disease or disorder to be treated is rheumatoid arthritis. In some embodiments, the disease or disorder to be treated is spondyloarthritis. In some embodiments, the disease or disorder to be treated is juvenile idiopathic arthritis. In some embodiments, the disease or disorder to be treated is osteoarthritis.

In some embodiments, the method of treatment provided herein is the treatment of one or more symptoms of a disease or disorder listed above.

Also provided herein is the use of a compound of the invention in therapy. In some embodiments, provided herein is the use of a compound of the invention for the treatment or prevention of the above diseases and disorders. Also provided herein is the use of a compound of the invention in the manufacture of a medicament for the treatment or prevention of the above diseases and disorders.

Also provided herein is a method of treating a disease or disorder as provided above in a mammal in need of such treatment, wherein the method comprises administering to said mammal a therapeutically effective amount of a compound of formula I, or a pharmaceutically acceptable salt thereof. In some embodiments, the mammal is a human.

Also provided herein is a method of treating a symptom of a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a disease or disorder in a human patient in need of such treatment, said disease or disorder being selected from those provided above, wherein the method comprises orally administering a therapeutically effective amount of a compound of formula I, or a pharmaceutically acceptable salt thereof, as an orally acceptable pharmaceutical composition.

Combination Therapy

Compounds of the invention may be combined with one or more other compounds of the invention or one or more other therapeutic agent as any combination thereof, in the treatment of the diseases and disorders provided herein. For example, a compound of the invention may be administered simultaneously, sequentially or separately in combination with other therapeutic agents known to be useful for the treatment of a disease or disorder selected from those recited above.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In some embodiments, a compound provided herein may be combined with another therapeutically active agent as recited in WO 2016/027253, the contents of which are hereby incorporated by reference in their entirety. In such embodiments, the compound that inhibits RIP1 kinase in the combinations recited in WO 2016/027253 is replaced by a compound of formula I of the present disclosure.

In some embodiments, a compound provided herein may be combined with a DLK inhibitor for the treatment of neurodegenerative diseases and disorders, such as those listed elsewhere herein, and including but not limited to the following: Parkinson's Disease, Lewy body dementia, multiple system atrophy, Parkinson-plus syndromes, Alzheimer's Disease, frontotemporal dementia, demyelination diseases such as multiple sclerosis, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, and corticobasal degeneration. DLK inhibitors are described, for example, in WO 2013/174780, WO 2014/177524, WO 2014/177060, WO 2014/111496, WO 2015/091889 and WO 2016/142310.

EXAMPLES

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated $CDCl_3$, $d_6$-DMSO, $CH_3OD$ or $d_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

All abbreviations used to describe reagents, reaction conditions or equipment are intended to be consistent with the definitions set forth in the following list of Abbreviations. The chemical names of discrete compounds of the invention were typically obtained using the structure naming feature of ChemDraw naming program.

ABBREVIATIONS

ACN Acetonitrile
Boc tert-Butoxycarbonyl
DAST Diethylaminosulfur trifluoride
DCE 1,2-dichloroethane
DCM Dichloromethane
DMF N,N-Dimethylformamide
DMSO Dimethyl sulfoxide
DPPH 2,2-Diphenyl-1-picrylhydrazyl
HPLC High Pressure Liquid Chromatography
LCMS Liquid Chromatography Mass Spectrometry
PCC Pyridinium chlorochromate
RP Reverse phase
RT or $R_T$ Retention time
SEM 2-(Trimethylsilyl)ethoxymethyl
SFC Supercritical Fluid Chromatography
TBDMS tert-Butyldimethylsilyl
TFA Trifluoroacetic acid
THF Tetrahydrofuran

Synthetic Schemes

In addition to the specific synthetic methods of the examples below, additional compounds of the present invention may be prepared, for example, according to the following synthetic schemes.

Schemes 1-4 illustrate the preparation of chemical intermediates provided in the examples herein. In addition, the bicyclic intermediates necessary for the preparation of compounds of Formula I (i.e., as represented by the A and B rings in Formula I) may be prepared according to the procedures described in WO 2017/004500 (the entirety of which is incorporated herein by reference).

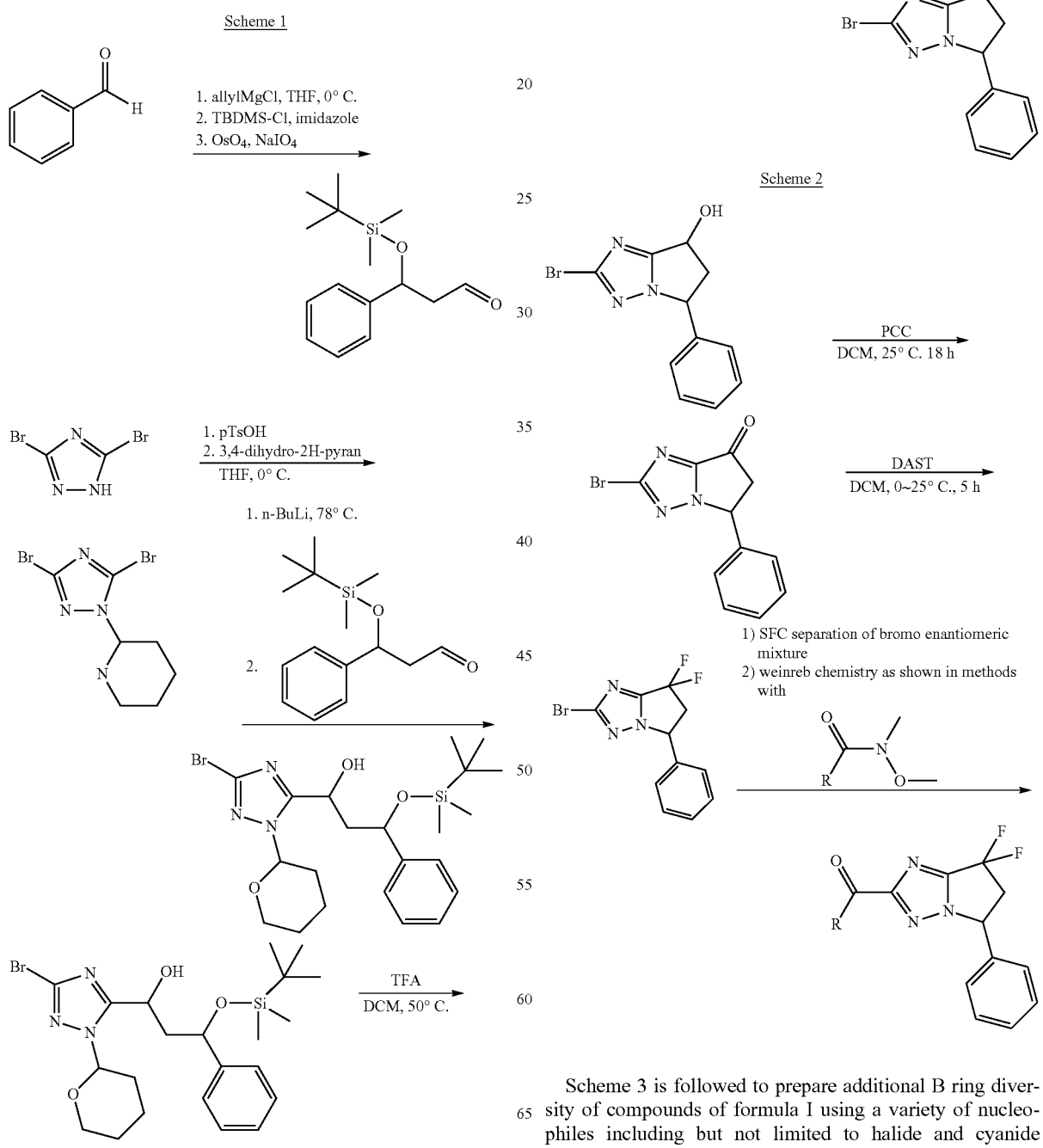

Scheme 3 is followed to prepare additional B ring diversity of compounds of formula I using a variety of nucleophiles including but not limited to halide and cyanide sources:

Scheme 3
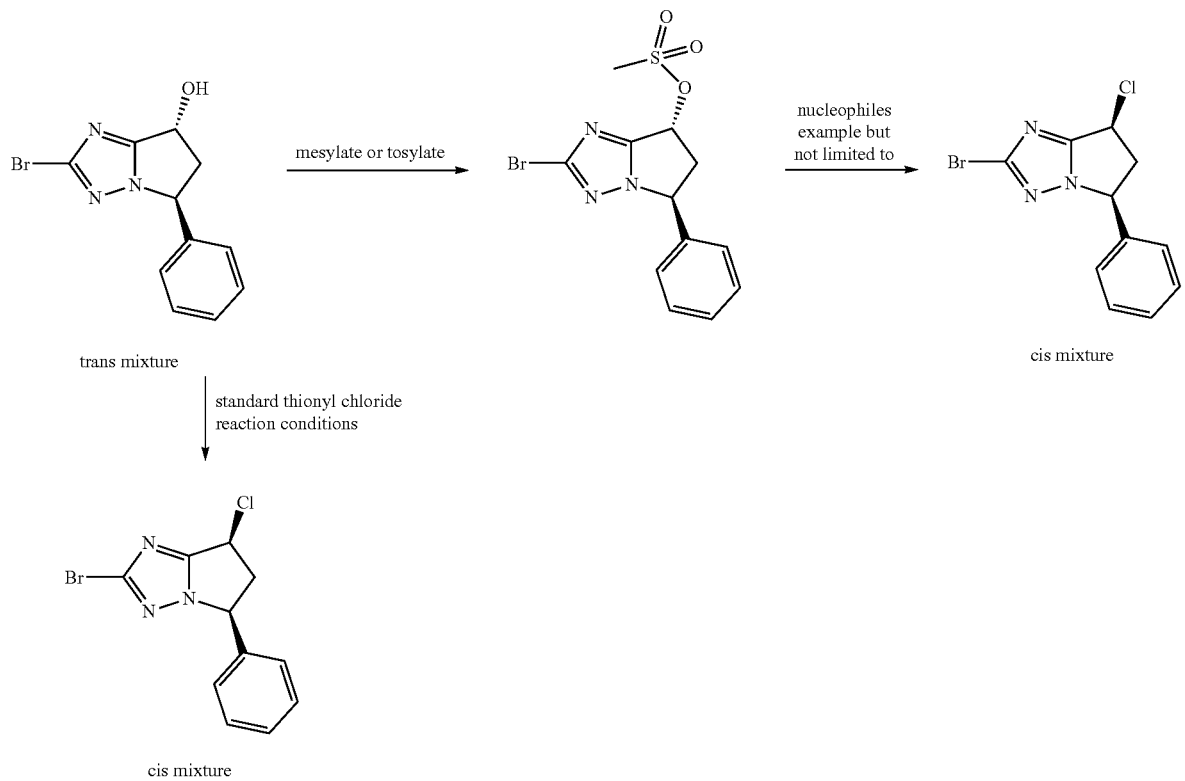
Scheme 4 is followed to prepare gem-dimethyl B ring substituted compounds of formula I:
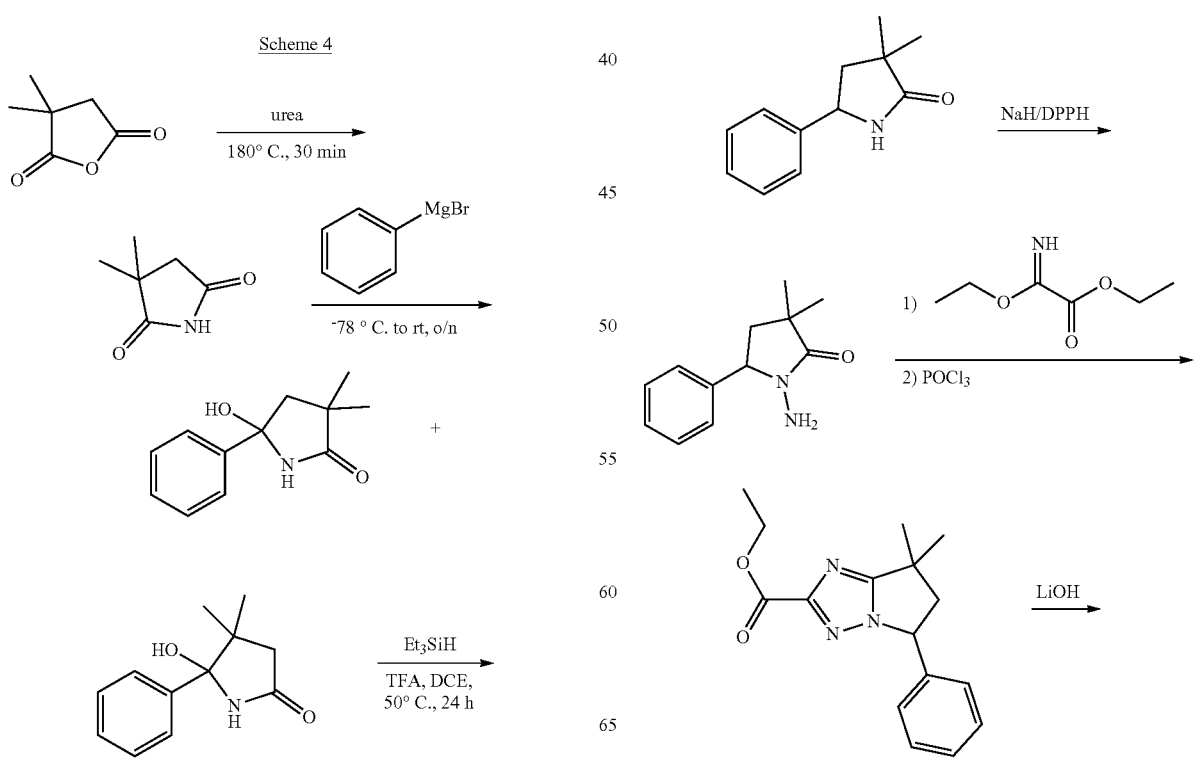

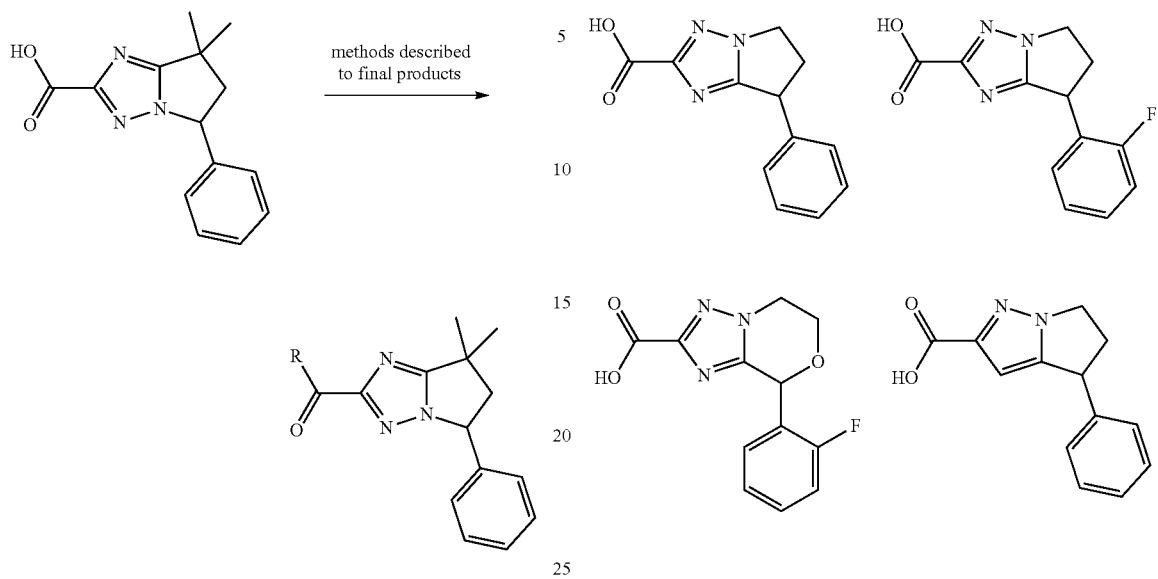
The following intermediates were prepared according to the procedures described in WO 2017/004500 (the entirety of which is incorporated herein by reference):
The following exemplary reactions are then used to prepare certain compounds of Formula I according to Scheme 5:
Scheme 5
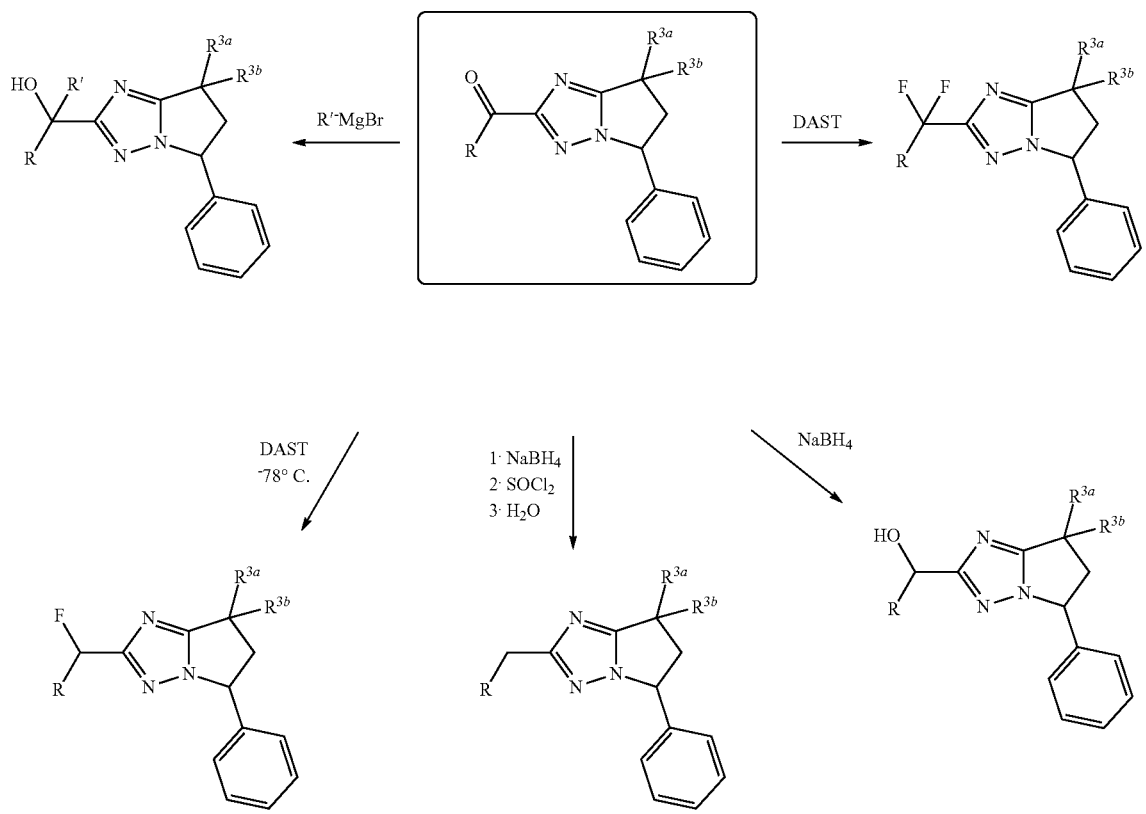

Exemplary Preparation of Mono-Fluorinated Intermediates

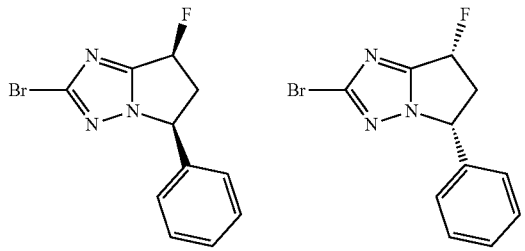 [SMILES: F[C@H]1C[C@@H](c2ccccc2)n2nc(Br)nc21 ; F[C@@H]1C[C@H](c2ccccc2)n2nc(Br)nc21]

Step 1: 3,5-dibromo-1-(tetrahydro-2H-pyran-2-yl)-1H-1,2,4-triazole

To a solution of 3,5-dibromo-1h-1,2,4-triazole (150.0 g, 661.2 mmol) in tetrahydrofuran (1500 mL) was slowly added p-toluenesulfonic acid (17.1 g, 99.2 mmol), followed by 3,4-dihydro-2h-pyran (166.9 g, 1983.6 mmol) at 0° C. After addition, the reaction mixture was heated at 70° C. for 3 h and concentrated under reduced pressure. The residue was poured into water (500 mL) and adjusted to pH=9 by addition of saturated aqueous sodium bicarbonate. The resulting mixture was extracted with ethyl acetate (3×400 mL). The combined organic layers were dried over sodium sulfate and concentrated under reduce pressure. The resulting crude product was washed with methanol (2×50 mL), dried under reduced pressure to give crude 3,5-dibromo-1-tetrahydropyran-2-yl-1,2,4-triazole (155 g, 75%) as a white solid. $^1$H NMR (400 MHz, CDCl$_3$) δ 5.49-5.46 (m, 1H), 4.12-3.99 (m, 1H), 3.72-3.61 (m, 1H), 2.38-2.26 (m, 1H), 2.18-2.07 (m, 1H), 1.98-1.90 (m, 1H), 1.78-1.60 (m, 3H).

Step 2: 1-phenylbut-3-en-1-ol

To a cooled (0° C.) solution of benzaldehyde (130 g, 1.23 mol) in tetrahydrofuran (1000 mL) was added allylmagnesium chloride (2 M in THF, 858 mL, 1.72 mol) over 30 min. After addition, the reaction mixture was allowed to warm to room temperature and stirred for 2 h. The mixture was then quenched by addition of saturated aqueous ammonium chloride (1000 mL) and extracted with ethyl acetate (3×500 mL). The combined organic layers were dried over sodium sulfate and concentrated under reduce pressure. The residue was purified by column chromatography (silica gel, 100-200 mesh, 0 to 5% ethyl acetate in petroleum ether) to give 1-phenylbut-3-en-1-ol (140 g, 77%) as a light yellow oil. $^1$H NMR (400 MHz, CDCl$_3$) δ 7.37-7.34 (m, 4H), 7.29-7.26 (m, 1H), 5.83-5.75 (m, 1H), 5.21-5.08 (m, 2H), 4.76-4.69 (m, 1H), 2.55-2.45 (m, 2H), 2.12 (d, J=2.8 Hz, 1H).

Step 3: tert-butyldimethyl((1-phenylbut-3-en-1-yl)oxy)silane

To a stirred solution of 1-phenyl-3-buten-1-ol (29.0 g, 195.7 mmol) in dichloromethane (400 mL) was added imidazole (27.0 g, 391.6 mmol) and tert-butyldimethylchlorosilane (39.0 g, 254.4 mmol). After addition, the reaction mixture was stirred at 25° C. for 16 h and then quenched by addition of water (200 mL). The mixture was extracted with dichloromethane (2×200 mL). The combined organic layers were washed with brine (100 mL), dried over sodium sulfate and concentrated under reduced pressure. The residue was purified by column chromatography (silica gel, 100-200 mesh, 100% petroleum ether) to afford tert-butyl-dimethyl-(1-phenylbut-3-enoxy)silane (43.0 g, 84%) as colorless oil, used as is in the next step.

Step 4: 3-((tert-butyldimethylsilyl)oxy)-3-phenylpropanal

To a solution of tert-butyl-dimethyl-(1-phenylbut-3-enoxy)silane (50.0 g, 190.5 mmol) in tetrahydrofuran/water (600 mL, 1:1) was added osmium tetraoxide (968 mg, 3.8 mmol). After stirring for 30 min at 15° C., sodium periodate (163 g, 762.0 mmol) was added in small portions over 2 h. The resulting mixture was stirred for another 2 h at 30° C. and then quenched by addition of cold saturated aqueous sodium thiosulfate (500 mL). The mixture was stirred for 30 min and then extracted with ethyl acetate (3×400 mL). The combined organic layers were washed with water (200 mL), brine (200 mL), dried over sodium sulfate and concentrated under reduced pressure. The residue was purified by column chromatography (silica gel, 100-200 mesh, 0 to 10% ethyl acetate in petroleum ether) to afford 3-[tert-butyl(dimethyl)silyl]oxy-3-phenyl-propanal (33.0 g, 65%) as yellow oil. $^1$H NMR (400 MHz, CDCl$_3$) δ 9.94 (t, J=2.4 Hz, 1H), 7.48 (d, J=4.2 Hz, 4H), 7.44-7.39 (m, 1H), 5.37-5.34 (m, 1H), 2.99-2.97 (m, 1H), 2.80-2.75 (m, 1H), 1.01 (s, 9H), 0.19 (s, 3H), 0.00 (s, 3H).

Step 5: 1-(3-bromo-1-(tetrahydro-2H-pyran-2-yl)-1H-1,2,4-triazol-5-yl)-3-((tert-butyldimethylsilyl)oxy)-3-phenylpropan-1-ol To a cooled (−78° C.) solution of 3,5-dibromo-1-tetrahydropyran-2-yl-1,2,4-triazole (39.0 g, 125.4 mmol) in tetrahydrofuran (400 mL) was added n-butyllithium (2.5 M in hexanes, 55.0 mL, 137.5 mmol) dropwise under N$_2$ atmosphere. The mixture was stirred at −78° C. for 30 min, then a solution of 3-[tert-butyl(dimethyl)silyl]oxy-3-phenyl-propanal (33.0 g, 124.2 mmol) in tetrahydrofuran (50 mL) was added dropwise. After addition, the mixture was stirred at −78° C. for 1.5 h and then quenched by addition of saturated aqueous ammonium chloride (500 mL). The resulting mixture was extracted with ethyl acetate (3×300 mL). The combined organic layers were dried over sodium sulfate and concentrated under reduce pressure. The residue was purified by column chromatography (silica gel, 100-200 mesh, 0 to 5% ethyl acetate in petroleum ether) to afford 1-(3-bromo-1-(tetrahydro-2H-pyran-2-yl)-1H-1,2,4-triazol-5-yl)-3-((tert-butyldimethylsilyl)oxy)-3-phenylpropan-1-ol (50.0 g, 80%) as light yellow oil.

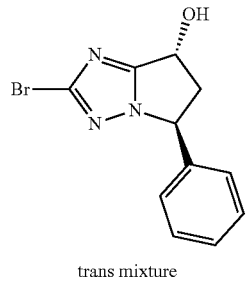 [SMILES: O[C@@H]1C[C@@H](c2ccccc2)n2nc(Br)nc21]

trans mixture

Step 6: trans-2-bromo-5-phenyl-6,7-dihydro-5H-pyrrolo[1,2-b][1,2,4]triazol-7-ol To a stirred solution of 1-(3-bromo-1-(tetrahydro-2H-pyran-2-yl)-1H-1,2,4-triazol-5-yl)-3-((tert-butyldimethylsilyl)oxy)-3-phenylpropan-1-ol (50.0 g, 100.7 mmol) in dichloromethane (150 mL) was slowly added trifluoroacetic acid (150 mL). The resulting mixture was heated at 50° C. for 2 h and then concentrated under reduced pressure. The residue was adjusted to pH=9 with saturated aqueous sodium bicarbonate and extracted with dichloromethane (3×200 mL). The combined organic layers were washed with water (100 mL), brine (100 mL), dried over sodium sulfate and concentrated under reduced pressure. The residue was purified by column chromatography (silica gel, 100-200 mesh, 0 to 32% ethyl acetate in petroleum ether) to afford trans-2-bromo-5-phenyl-6,7-dihydro-5H-pyrrolo[1,2-b][1,2,4]triazol-7-ol (5.5 g, 20%) as a yellow solid (A second fraction (8.5 g, 30%) was also obtained as a 4:3 mixture of trans/cis products). $^1$H NMR (400 MHz, CDCl$_3$) δ 7.46-7.32 (m, 3H), 7.15 (d, J=7.6 Hz, 2H), 5.65 (t, J=6.6 Hz, 1H), 5.50 (br s, 1H), 5.45 (d, J=6.4 Hz, 1H), 3.19-3.11 (m, 1H), 3.01-2.92 (m, 1H). LCMS RT=0.682 min, m/z=279.8 [M+H]$^+$. LCMS (5 to 95% acetonitrile in water+ 0.03% trifluoroacetic acid over 1.5 mins) retention time 0.682 min, ESI+ found [M+H]=279.8.

Step 7: (5S,7S)-2-bromo-7-fluoro-5-phenyl-6,7-dihydro-5H-pyrrolo[1,2-b][1,2,4]triazole and (5R,7R)-2-bromo-7-fluoro-5-phenyl-6,7-dihydro-5H-pyrrolo[1,2-b][1,2,4]triazole To a stirred solution of trans-2-bromo-5-phenyl-6,7-dihydro-5H-pyrrolo[1,2-b][1,2,4]triazol-7-ol (3.0 g, 10.71 mmol) in dichloromethane (60 mL) was slowly added diethylaminosulfur trifluoride (7.8 g, 48.19 mmol) at 0° C. The reaction mixture was stirred at 0° C. for 2.5 h and then slowly added into stirred aqueous saturated sodium bicarbonate (100 mL) at 0° C. The mixture was extracted with dichloromethane (3×100 mL). The combined organic layers were washed with water (100 mL), brine (100 mL), dried over sodium sulfate and concentrated under reduced pressure. The residue was purified by column chromatography (silica gel, 100-200 mesh, 0 to 20% ethyl acetate in petroleum ether) to afford racemic cis-2-bromo-7-fluoro-5-phenyl-6,7-dihydro-5H-pyrrolo[1,2-b][1,2,4]triazole (1.5 g, 49%) as a light yellow solid and racemic trans-2-bromo-7-fluoro-5-phenyl-6,7-dihydro-5H-pyrrolo[1,2-b][1,2,4]triazole (650 mg, 21%) as a white solid.

cis-2-bromo-7-fluoro-5-phenyl-6,7-dihydro-5H-pyrrolo[1,2-b][1,2,4]triazole: $^1$H NMR (400 MHz, CDCl$_3$) δ 7.31-7.24 (m, 3H), 7.17-7.07 (m, 2H), 5.97-5.77 (m, 1H), 5.37-5.27 (m, 1H), 3.52-3.37 (m, 1H), 2.84-2.70 (m, 1H). LCMS R$_T$=0.632 min, m/z=281.9 [M+H]$^+$. LCMS (5 to 95% acetonitrile in water+0.03% trifluoroacetic acid over 1.5 mins) retention time 0.632 min, ESI+ found [M+H]=281.9.

trans-2-bromo-7-fluoro-5-phenyl-6,7-dihydro-5H-pyrrolo[1,2-b][1,2,4]triazole: $^1$H NMR (400 MHz, CDCl$_3$) δ 7.58-7.29 (m, 3H), 7.24-7.05 (m, 2H), 6.14-5.93 (m, 1H), 5.70-5.65 (m, 1H), 3.41-3.25 (m, 1H), 3.04-2.87 (m, 1H).

The racemic cis material was further separated by chiral SFC to give arbitrarily assigned:
(5R,7R)-2-bromo-7-fluoro-5-phenyl-6,7-dihydro-5H-pyrrolo[1,2-b][1,2,4]triazole (Peak 1, retention time=2.963 min) (350 mg, 44%) as a white solid.

(5S,7S)-2-bromo-7-fluoro-5-phenyl-6,7-dihydro-5H-pyrrolo[1,2-b][1,2,4]triazole (Peak 2, retention time=3.174 min) (350 mg, 44%) as a white solid.

SFC condition: Column: Chiralpak AD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min.

Example 1

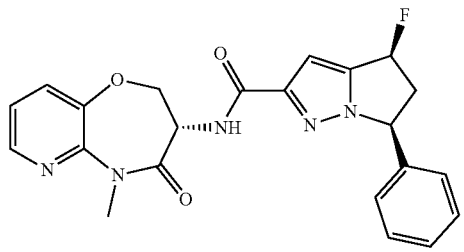

(4S,6S)-4-fluoro-6-phenyl-N-[(3S)-5-methyl-4-oxo-2,3-dihydropyrido[3,2-b][1,4]oxazepin-3-yl]-5,6-dihydro-4H-pyrrolo[1,2-b]pyrazole-2-carboxamide

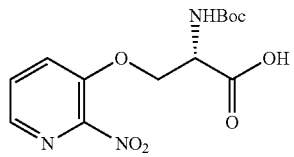 [SMILES: CC(C)(C)OC(=O)N[C@@H](COc1cccnc1[N+](=O)[O-])C(=O)O]

Step 1: (2S)-2-(((tert-butoxy)carbonyl)amino)-3-((2-nitropyridin-3-yl)oxy)propanoic acid Sodium hydride (60%, 2.0 g, 51.17 mmol) was added into a stirred solution of (2S)-2-(tert-butoxycarbonylamino)-3-hydroxypropanoic acid (5.0 g, 25.0 mmol) in N,N-dimethylformamide (100 mL). The resulting mixture was stirred at 0° C. for 2 hours and 3-fluoro-2-nitropyridine (3.6 g, 25.3 mmol) was added. The reaction mixture was stirred at room temperature for additional 8 h and quenched by addition of aqueous hydrochloric acid (3 N, 5 mL). The mixture was adjusted to pH=3-4 with aqueous hydrochloric acid (3N, 20 mL) and extracted with ethyl acetate (3×100 mL). The combined organic layers were washed with brine, dried over anhydrous sodium sulfate and concentrated under reduced pressure. The residue was purified by RP-HPLC (acetonitrile 5-55/0.225% formic acid in water) to afford (2S)-2-(tert-butoxycarbonylamino)-3-[(2-nitro-3-pyridyl)oxy]propanoic acid (4.2 g, 53%) as a yellow solid.

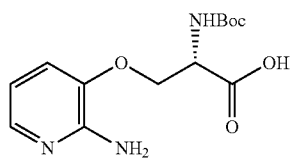

Step 2: (2S)-3-((2-aminopyridin-3-yl)oxy)-2-(((tert-butoxy)carbonyl)amino)propanoic acid A mixture of (2S)-2-(((tert-butoxy)carbonyl)amino)-3-((2-nitropyridin-3-yl)oxy) propanoic acid (3.0 g, 9.17 mmol) and palladium (10% on carbon, 3.0 g) in methanol (50 mL) was hydrogenated (40 psi) at room temperature for 12 h and then filtered through a small pad of Celite. The filtrate was concentrated under reduced pressure to afford the crude (2S)-3-((2-aminopyridin-3-yl)oxy)-2-(((tert-butoxy)carbonyl) amino)propanoic acid (1.5 g, 55%) as a yellow oil use without further purification in the next step. LCMS $R_T$=0.488 min, m/z=297.9 [M+H]$^+$.

LCMS (5 to 95% acetonitrile in water+0.03% trifluoacetic acid over 1.5 mins) retention time 0.488 min, ESI+ found [M+H]=297.9.

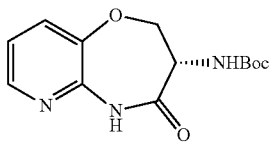 [SMILES: CC(C)(C)OC(=O)N[C@H]1COc2cccnc2NC1=O]

Step 3: tert-butyl (S)-(4-oxo-2,3,4,5-tetrahydropyrido[3,2-b][1,4]oxazepin-3-yl)carbamate A mixture of (2S)-3-((2-aminopyridin-3-yl)oxy)-2-(((tert-butoxy)carbonyl)amino) propanoic acid (1.5 g, 5.05 mmol), N,N-diisopropylethylamine (1.3 g, 10.9 mmol) and N,N,N',N'-tetramethyl-O-(7-azabenzotriazol-1-yl)uronium hexafluorophospate (2.9 g, 7.57 mmol) in N,N-dimethylformamide (20 mL) was stirred for 6 h at room temperature and then quenched by the addition of water (20 mL). The mixture was extracted with ethyl acetate (2×70 mL). The combined organic layers were washed with brine, dried over anhydrous sodium sulfate and concentrated under reduced pressure. The residue was purified by column chromatography (silica gel, 100-200 mesh, 0 to 10% methanol in dichloromethane) to afford tert-butyl (S)-(4-oxo-2,3,4,5-tetrahydropyrido[3,2-b][1,4]oxazepin-3-yl)carbamate (900 mg, 64%) as a yellow solid. LCMS $R_T$=0.720 min, m/z=280.0 [M+H]$^+$.

LCMS (5 to 95% acetonitrile in water+0.03% trifluoacetic acid over 1.5 mins) retention time 0.720 min, ESI+ found [M+H]=280.0.

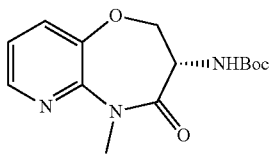 [SMILES: CN1C(=O)[C@@H](NC(=O)OC(C)(C)C)COc2cccnc21]

Step 4: tert-butyl (S)-(5-methyl-4-oxo-2,3,4,5-tetrahydropyrido[3,2-b][1,4]oxazepin-3-yl)carbamate Iodomethane (0.13 mL, 2.11 mmol) was added dropwise to a stirring solution of tert-butyl N-((3S)-4-oxo-2H,3H,4H,5H-pyrido[3,2-b][1,4]oxazepin-3-yl)carbamate (590 mg, 2.11 mmol) and cesium carbonate (690 mg, 2.12 mmol) in N,N-dimethylformamide (5 mL). The reaction mixture was stirred for 3 h at room temperature and diluted with water (20 mL). The mixture was then extracted with ethyl acetate (3×20 mL). The combined organic layers were washed with brine, dried over anhydrous sodium sulfate, filtered and concentrated under reduced pressure. The residue was purified by column chromatography (silica gel, 100-200 mesh, 0 to 40% ethyl acetate in petroleum ether) to afford tert-butyl (S)-(5-methyl-4-oxo-2,3,4,5-tetrahydropyrido[3,2-b][1,4] oxazepin-3-yl)carbamate (350 mg, 57%) as a yellow solid. LCMS $R_T$=0.761 min, m/z=294.1 [M+H]$^+$.

LCMS (5 to 95% acetonitrile in water+0.03% trifluoacetic acid over 1.5 mins) retention time 0.761 min, ESI+ found [M+H]=294.1.

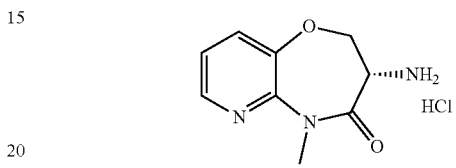

Step 5: (S)-3-amino-5-methyl-2,3-dihydropyrido[3,2-b][1,4]oxazepin-4(5H)-one hydrochloride tert-butyl (S)-(5-methyl-4-oxo-2,3,4,5-tetrahydropyrido [3,2-b][1,4]oxazepin-3-yl)carbamate (350 mg, 1.19 mmol) was added to a solution of hydrogen chloride in dioxane (4.0 M, 10 mL). The reaction mixture was stirred for 3 h at room temperature and concentrated under reduced pressure to afford the crude ((S)-3-amino-5-methyl-2,3-dihydropyrido [3,2-b][1,4]oxazepin-4(5H)-one hydrochloride (400 mg, 99%) as a white solid. LCMS $R_T$=0.360 min, m/z=194.1 [M+H]$^+$.

LCMS (5 to 95% acetonitrile in water+0.03% trifluoacetic acid over 1.5 mins) retention time 0.360 min, ESI+ found [M+H]=194.1.

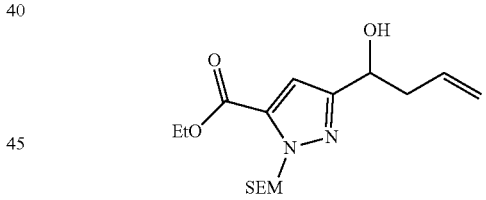

Step 6: ethyl 3-(1-hydroxybut-3-en-1-yl)-1-((2-(trimethylsilyl)ethoxy)methyl)-1H-pyrazole-5-carboxylate To a solution of ethyl 5-formyl-2-(2-trimethylsilylethoxymethyl)pyrazole-3-carboxylate (40.0 g, 134.0 mmol) in dichloromethane (400 mL) and water (400 mL) was added tetrabutylammonium iodide (4.95 g, 13.4 mmol) and potassium allyltrifluoroborate (39.7 g, 268.1 mmol). After addition, the mixture was stirred at 25° C. for 2 h and diluted with water (200 mL). The resulting mixture was extracted with dichloromethane (3×200 mL). The combined organic layers were washed with water (100 mL), brine (300 mL), dried over anhydrous magnesium sulfate and concentrated under reduced pressure to afford crude ethyl 5-(1-hydroxybut-3-enyl)-2-(2-trimethylsilylethoxymethyl)pyrazole-3-carboxylate (45.0 g, 99%) as a yellow oil. This crude was used for the next step reaction without further purification.

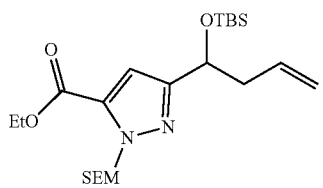 [SMILES: C=CCC(O[Si](C)(C)C(C)(C)C)c1cc(C(=O)OCC)n(COCC[Si](C)(C)C)n1]

Step 7: ethyl 3-(1-((tert-butyldimethylsilyl)oxy)but-3-en-1-yl)-1-((2-(trimethylsilyl)ethoxy)methyl)-1H-pyrazole-5-carboxylate To a solution of ethyl 5-(1-hydroxybut-3-enyl)-2-(2-trimethylsilylethoxymethyl)pyrazole-3-carboxylate (47.0 g, 138.04 mmol) in dichloromethane (400 mL) was added imidazole (28.2 g, 414.11 mmol) and tert-butyldimethylchlorosilane (31.2 g, 207.05 mmol). The reaction mixture was stirred at 25° C. for 16 h. The mixture was then washed with water (100 mL), brine (100 mL), dried over anhydrous magnesium sulfate and concentrated under reduced pressure. The residue was purified by column chromatography (silica gel, 100-200 mesh, 0 to 10% ethyl acetate in petroleum ether) to afford ethyl 5-[1-[tert-butyl(dimethyl)silyl]oxybut-3-enyl]-2-(2-trimethylsilylethoxymethyl)pyrazole-3-carboxylate (43.0 g, 69%) as a colorless oil. $^1$H NMR (400 MHz, CDCl$_3$) δ 6.87 (s, 1H), 5.83-5.76 (m, 3H), 5.06-5.02 (m, 2H), 4.86-4.83 (m, 1H), 4.38-4.35 (m, 2H), 3.57-3.53 (m, 2H), 1.39 (t, J=7.2 Hz, 3H), 0.87 (s, 9H), 0.06 (s, 3H), 0.06-0.05 (m, 12H).

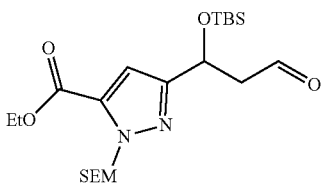 [SMILES: CCOC(=O)c1cc(C(CC=O)O[Si](C)(C)C(C)(C)C)nn1COCC[Si](C)(C)C]

Step 8: ethyl 3-(1-((tert-butyldimethylsilyl)oxy)-3-oxopropyl)-1-((2-(trimethylsilyl)ethoxy)methyl)-1H-pyrazole-5-carboxylate To a solution of ethyl 5-[1-[tert-butyl(dimethyl)silyl]oxybut-3-enyl]-2-(2-trimethylsilylethoxymethyl)pyrazole-3-carboxylate (40.0 g, 88.0 mmol) in water (400 mL) and tetrahydrofuran (400 mL) was added osmium tetroxide (1.5 g, 5.9 mmol). After stirred for 40 min at 25° C., sodium periodate (75.3 g, 351.8 mmol) was added in small portions over 2 h. The resulting mixture was stirred for 1 h at 25° C. and filtered. The filtrate was diluted with saturated aqueous sodium thiosulfate (500 mL) and extracted with ethyl acetate (3×500 mL). The combined organic layers were washed with water (300 mL), brine (300 mL), dried over anhydrous magnesium sulfate and concentrated under reduced pressure. The residue was purified by column chromatography (silica gel, 100-200 mesh, 0 to 20% ethyl acetate in petroleum ether) to give ethyl 3-(1-((tert-butyldimethylsilyl)oxy)-3-oxopropyl)-1-((2-(trimethylthoxy)methyl)-1H-pyrazole-5-carboxylate (21.0 g, 52%) as a colorless oil. $^1$H NMR (400 MHz, CDCl$_3$) δ 9.82-9.81 (m, 1H), 6.88 (s, 1H), 5.83 (d, J=10.4, 1H), 8.76 (d, J=10.4, 1H), 5.37-5.35 (m, 1H), 4.38-4.34 (m, 2H), 3.58-3.54 (m, 2H), 2.90-2.88 (m, 1H), 2.87-2.76 (m, 1H), 1.41-1.37 (m, 3H), 0.88 (s, 1H), 0.09 (s, 3H), −0.03 (s, 3H), −0.04-−0.05 (s, 9H).

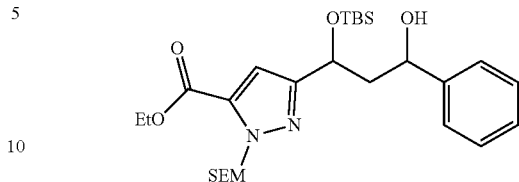

Step 9: ethyl 3-(1-((tert-butyldimethylsilyl)oxy)-3-hydroxy-3-phenylpropyl)-1-((2-(trimethylsilyl)ethoxy)methyl)-1H-pyrazole-5-carboxylate To a solution of ethyl 5-[1-[tert-butyl(dimethyl)silyl]oxy-3-oxo-propyl]-2-(2-trimethylsilylethoxymethyl)pyrazole-3-carboxylate (11.0 g, 24.08 mmol) in tetrahydrofuran (250 mL) was added phenylmagnesium bromide (1.0 M in n-hexane, 28.9 mL, 28.90 mmol) over 30 min at −78° C. After stirred at 0° C. for 2 h, the mixture was quenched by addition of saturated ammonium chloride solution (100 mL) and extracted with ethyl acetate (3×100 mL). The combined organic layers were washed with brine (80 mL), dried over anhydrous magnesium sulfate and concentrated under reduced pressure. The crude product was purified by column chromatography (silica gel, 100-200 mesh, 0 to 20% ethyl acetate in petroleum ether) to give ethyl 5-[1-[tert-butyl(dimethyl)silyl]oxy-3-hydroxy-3-phenyl-propyl]-2-(2-trimethylsilylethoxymethyl)pyrazole-3-carboxylate (11.5 g, 89%) as a yellow oil.

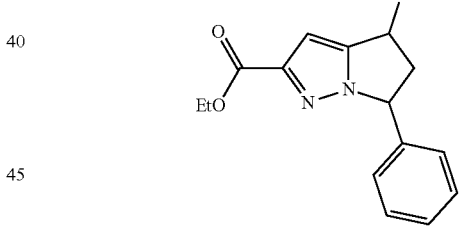

Step 10: ethyl 4-hydroxy-6-phenyl-5,6-dihydro-4H-pyrrolo[1,2-b]pyrazole-2-carboxylate A mixture of ethyl 3-(1-((tert-butyldimethylsilyl)oxy)-3-hydroxy-3-phenylpropyl)-1-((2-(trimethylsilyl)ethoxy)methyl)-1H-pyrazole-5-carboxylate (11.5 g, 21.5 mmol) in trifluoroacetic acid (97.7 mL) was stirred at 55° C. for 2 h. The mixture was concentrated under reduced pressure and the residue was purified by a column chromatography (silica gel, 100-200 mesh, 0 to 40% ethyl acetate in petroleum ether) to give ethyl 4-hydroxy-6-phenyl-5,6-dihydro-4H-pyrrolo[1,2-b]pyrazole-2-carboxylate (4.1 g, 70%) as a yellow oil. LCMS R$_T$=0.734 min, m/z=273.1 [M+H]$^+$.

LCMS (5 to 95% acetonitrile in water+0.1% formic acid over 1.5 mins) retention time 0.734 min, ESI+ found [M+H]=273.1.

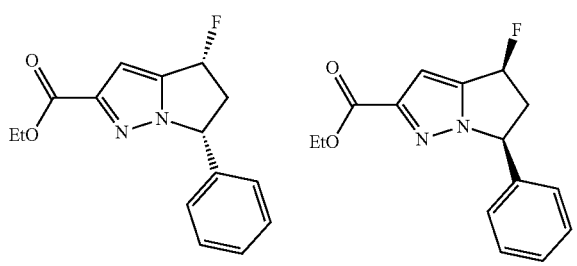 [SMILES: CCOC(=O)c1cc2n(n1)[C@@H](c1ccccc1)C[C@H]2F ; CCOC(=O)c1cc2n(n1)[C@H](c1ccccc1)C[C@@H]2F]

Step 11: (4R,6R)-ethyl 4-fluoro-6-phenyl-5,6-di-hydro-4H-pyrrolo[1,2-b]pyrazole-2-carboxylate and (4S,6S)-ethyl 4-fluoro-6-phenyl-5,6-dihydro-4H-pyrrolo[1,2-b]pyrazole-2-carboxylate To a solution of ethyl-hydroxy-6-phenyl-5,6-dihydro-4H-pyrrolo[1,2-b]pyrazole-2-carboxylate (2.2 g, 8.08 mmol) in dichloromethane (50 mL) was slowly added diethylaminosulfur trifluoride (5.2 g, 32.32 mmol) at 0° C. After stirred at 0° C. for 2 h, the mixture was quenched by addition of saturated aqueous sodium bicarbonate and extracted with dichloromethane (3×50 mL). The combined organic layers were washed with brine (50 mL), dried and concentrated to dryness under reduced pressure. The residue was purified by column chromatography (silica gel, 100-200 mesh, 0 to 30% ethyl acetate in petroleum ether) to afford ethyl cis-4-fluoro-6-phenyl-5,6-dihydro-4H-pyrrolo[1,2-b]pyrazole-2-carboxylate (500 mg, 23%) as a yellow oil.

This material was further separated by chiral SFC to give arbitrarily assigned (4R,6R)-ethyl 4-fluoro-6-phenyl-5,6-dihydro-4H-pyrrolo[1,2-b]pyrazole-2-carboxylate (Peak 1, retention time 2.641 min) (140 mg, 28%) and ethyl (4S,6S)-4-fluoro-6-phenyl-5,6-dihydro-4H-pyrrolo[1,2-b]pyrazole-2-carboxylate (Peak 2, retention time 3.400 min) (160 mg, 32%), both as yellow oil.

SFC conditions: Chiralpak AD 250×30 mm I.D., 5 um; Supercritical CO2/EtOH+0.1% NH3.H2O=25/75; 50 mL/min. Column temp.: 40° C.

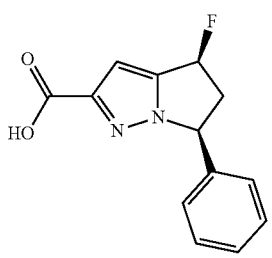 [SMILES: O=C(O)c1cc2n(n1)[C@H](c1ccccc1)C[C@@H]2F]

Step 12: (4S,6S)-4-fluoro-6-phenyl-5,6-dihydro-4H-pyrrolo[1,2-b]pyrazole-2-carboxylic acid A mixture of ethyl (4S,6S)-4-fluoro-6-phenyl-5,6-dihydro-4H-pyrrolo[1,2-b]pyrazole-2-carboxylate (160 mg, 0.58 mmol) and lithium hydroxide monohydrate (122 mg, 2.92 mmol) in tetrahydrofuran (5 mL), methanol (1 mL) and water (1 mL) was stirred at 20° C. for 16 h. The mixture was adjusted to pH=5 by addition of aqueous hydrochloric acid (1 M) and concentrated under reduced pressure. The residue was added a mixture of 10% methanol in dichloromethane (20 mL) and filtered. The filtrate was concentrated under reduced pressure to give the crude (4R,6R)-4-fluoro-6-phenyl-5,6-dihydro-4H-pyrrolo[1,2-b]pyrazole-2-carboxylic acid (120 mg, 84%) as a white solid. This crude was used directly for next step.

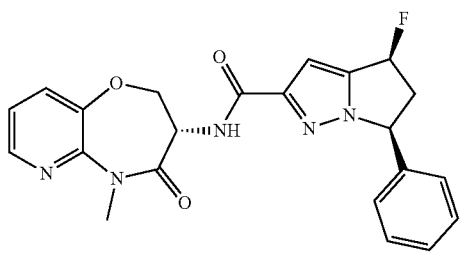

Step 13: (4S,6S)-4-fluoro-6-phenyl-N-[(3S)-5-methyl-4-oxo-2,3-dihydropyrido[3,2-b][1,4]oxazepin-3-yl]-5,6-dihydro-4H-pyrrolo[1,2-b]pyrazole-2-carboxamide A mixture of 1-hydroxybenzotriazole (4.9 mg, 0.04 mmol), (3S)-3-amino-5-methyl-2,3-dihydropyrido[3,2-b][1,4]oxazepin-4-one hydrochloride (63.0 mg, 0.27 mmol), (4S,6S)-4-fluoro-6-phenyl-5,6-dihydro-4H-pyrrolo[1,2-b]pyrazole-2-carboxylic acid (45.0 mg, 0.18 mmol), 1-(3-dimethylaminopropyl)-3-ethylcarbodiimidehydrochloride (52.6 mg, 0.27 mmol) and N,N-diisopropylethylamine (0.08 mL, 0.46 mmol) in N,N-dimethylformamide (1 mL) was stirred at 25° C. for 16 h. The mixture was concentrated under reduced pressure and the residue was purified by chiral SFC (Column: DAICEL CHIRALCEL OD(250 mm*30 mm, 10 um), 0.1% $NH_3H_2O$. EtOH, Begin B 35%, End B 35%, FlowRate: 80 mL/min) to afford (4S,6S)-4-fluoro-6-phenyl-N-[(3S)-5-methyl-4-oxo-2,3-dihydropyrido[3,2-b][1,4]oxazepin-3-yl]-5,6-dihydro-4H-pyrrolo[1,2-b]pyrazole-2-carboxamide (13 mg, 17%) as a white solid. $^1H$ NMR (400 MHz, $CDCl_3$) δ 8.23-8.20 (m, 1H), 7.67-7.64 (m, 1H), 7.45-7.41 (m, 1H), 7.32-7.17 (m, 3H), 7.12-7.05 (m, 3H), 6.82-6.80 (m, 1H), 5.98-5.81 (m, 1H), 5.37-5.32 (m, 1H), 4.96-4.90 (m, 1H), 4.76-4.70 (m, 1H), 4.21 (t, J=6.0 Hz, 1H), 3.50-3.25 (m, 4H), 2.79-2.67 (m, 1H). LCMS $R_T$=0.863 min, m/z=422.1 [M+H]$^+$. LCMS (5 to 95% acetonitrile in water+0.03% trifluoacetic acid over 1.5 mins) retention time 0.863 min, ESI+ found [M+H]=422.1.

Example 2

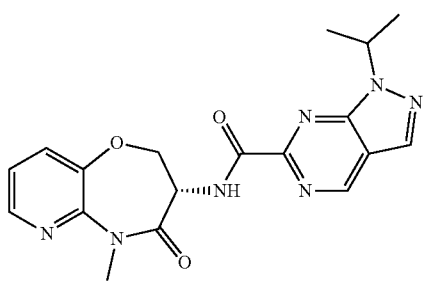 [SMILES: CC(C)n1ncc2cnc(C(=O)N[C@H]3COc4cccnc4N(C)C3=O)nc21]

1-isopropyl-N-[(3S)-5-methyl-4-oxo-2,3-dihydro-pyrido[3,2-b][1,4]oxazepin-3-yl]pyrazolo[3,4-d]pyrimidine-6-carboxamide A mixture of (3S)-3-amino-5-methyl-2,3-dihydropyrido[3,2-b][1,4]oxazepin-4-one hydrochloride (89.4 mg, 0.39 mmol), 1-hydroxybenzotriazole (45.9 mg, 0.34 mmol), 1-(3-dimethylaminopropyl)-3-ethylcarbodiimidehydrochloride (65.1 mg, 0.34 mmol) and 1-isopropylpyrazolo[3,4-d]pyrimidine-6-carboxylic acid (70.0 mg, 0.34 mmol) in N,N-dimethylformamide (2 mL) was stirred at 10° C. for 20 h. The mixture was diluted with water (15 mL) and extracted with ethyl acetate (3×15 mL). The combined organic layers were concentrated under reduced pressure and the residue was purified by RP-HPLC (acetonitrile 20-50/0.05% ammonia hydroxide in water) to afford 1-isopropyl-N-[(3S)-5-methyl-4-oxo-2,3-dihydropyrido[3,2-b][1,4]oxazepin-3-yl]pyrazolo[3,4-d]pyrimidine-6-carboxamide (44.7 mg, 34%) as a white solid. NMR (400 MHz, CD$_3$OD) δ 9.36 (s, 1H), 8.39-8.35 (m, 2H), 7.71-7.69 (m, 1H), 7.35-7.32 (m, 1H), 5.45-5.42 (m, 1H), 5.11-5.09 (m, 1H), 4.81-4.77 (m, 1H), 4.63-4.53 (m, 1H), 3.51 (s, 3H), 1.60 (d, J=6.4 Hz, 6H). LCMS R$_T$=0.958 min, m/z=382.2 [M+H]$^+$.

LCMS (10 to 80% acetonitrile in water+0.03% trifluoacetic acid over 2.0 mins) retention time 0.958 min, ESI+ found [M+H]=383.2.

Examples 3 and 4

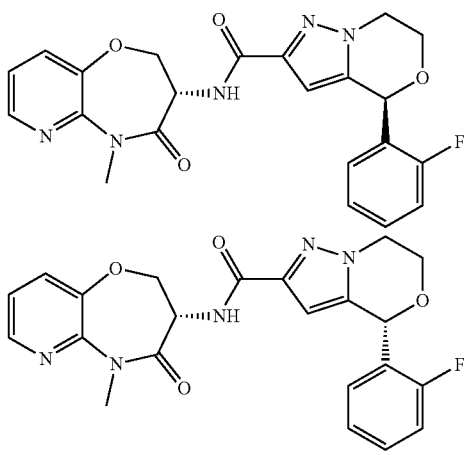

(4S)-4-(2-fluorophenyl)-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide and (4R)-4-(2-fluorophenyl)-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide A mixture of (3S)-3-amino-5-methyl-2,3-dihydropyrido[3,2-b][1,4]oxazepin-4-one hydrochloride (70.0 mg, 0.30 mmol), 4-(2-fluorophenyl)-6,7-dihydro-4H-pyrazolo[5,1-c][1,4]oxazine-2-carboxylic acid (90.0 mg, 0.34 mmol), 1-(3-dimethylaminopropyl)-3-ethylcarbodiimidehydrochloride (129.0 mg, 0.67 mmol), 1-hydroxybenzotriazole (91.0 mg, 0.67 mmol) and N,N-diisopropylethylamine (158.0 mg, 1.22 mmol) in N,N-dimethylformamide (3 mL) was stirred at 15° C. for 16 h. The reaction mixture was diluted with water (50 mL) and extracted with ethyl acetate (2×30 mL). The combined organic layers were washed with brine (2×30 mL), dried over sodium sulfate and concentrated under reduced pressure. The residue was purified by preparative TLC (70% ethyl acetate in petroleum ether) to afford 4-(2-fluorophenyl)-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide (60 mg, 45%) as a colorless oil. LCMS R$_T$=0.696 min, m/z=438.0 [M+H]$^+$.

LCMS (5 to 95% acetonitrile in water+0.03% trifluoacetic acid over 1.5 mins) retention time 0.696 min, ESI+ found [M+H]=438.0.

This racemic material was further separated by SFC to afford arbitrarily assigned:

(4S)-4-(2-fluorophenyl)-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide (peak 1, retention time=3.607 min) (21.8 mg, 35% yield) as a white solid. $^1$H NMR (400 MHz, CDCl$_3$) δ 8.31-8.30 (m, 1H), 7.83-7.80 (m, 1H), 7.52 (d, J=8.0 Hz, 1H), 7.30-7.27 (m, 2H), 7.20-7.13 (m, 3H), 6.33 (s, 1H), 6.08 (s, 1H), 5.05-5.02 (m, 1H), 4.82-4.77 (m, 1H), 4.42-4.40 (m, 2H), 4.34-4.28 (m, 2H), 4.17-4.10 (m, 1H), 3.54 (s, 3H). LCMS RT=0.844 min, m/z=438.1 [M+H]$^+$ LCMS (5 to 95% acetonitrile in water+0.03% trifluoacetic acid over 1.5 mins) retention time 0.844 min, ESI+ found [M+H]=438.1.

(4R)-4-(2-fluorophenyl)-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide (peak 2, retention time=3.906 min) (21.1 mg, 35%) as a white solid. $^1$H NMR (400 MHz, CDCl$_3$) δ 8.31 (d, J=4.8 Hz, 1H), 7.83-7.81 (m, 1H), 7.52 (dd, J=1.6, 8.0 Hz, 1H), 7.40-7.30 (m, 2H), 7.20-7.12 (m, 3H), 6.33 (s, 1H), 6.09 (s, 1H), 5.05-5.02 (m, 1H), 4.82-4.78 (m, 1H), 4.43-4.40 (m, 2H), 4.35-4.29 (m, 2H), 4.20-4.16 (m, 1H), 3.54 (s, 3H). LCMS RT=0.840 min, m/z=438.1 [M+H]$^+$.

LCMS (5 to 95% acetonitrile in water+0.03% trifluoacetic acid over 1.5 mins) retention time 0.840 min, ESI+ found [M+H]=438.1.

SFC condition: Column: AD (250 mm*30 mm, 5 um), Mobile phase: A: CO2 B: methanol (0.1% NH$_3$H$_2$O) Gradient: from 5% to 40% of B, Column temp.: 15° C.

Example 5

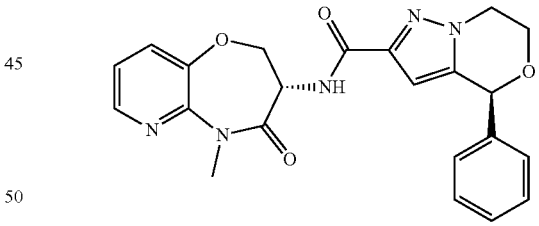

(4S)-4-phenyl-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide A mixture of (3S)-3-amino-5-methyl-2,3-dihydropyrido[3,2-b][1,4]oxazepin-4-one hydrochloride (58.0 mg, 0.25 mmol), 1-(3-dimethylaminopropyl)-3-ethylcarbo diimidehydrochloride (106.5 mg, 0.56 mmol), (4S)-4-phenyl-6,7-dihydro-4h-pyrazolo[5,1-C][1,4]oxazine-2-carboxylic acid (123.4 mg, 0.51 mmol), N,N-diisopropylethylamine (0.18 mL, 1.01 mmol) and 1-hydroxybenzotriazole (75.1 mg, 0.56 mmol) in N,N-dimethylformamide (0.5 ml) was stirred at 15° C. for 4 h and concentrated under reduced pressure. The residue was purified by RP-HPLC (acetonitrile 29-59%/

0.05% ammonium bicarbonate in water) to afford (4S)-4-phenyl-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide (21.2 mg, 18%) as a yellow solid. $^{1}$H NMR (400 MHz, CD$_{3}$OD) δ 8.33-8.32 (m, 1H), 7.66-7.64 (m, 1H), 7.37 (s, 5H), 7.31-7.27 (m, 1H), 6.18 (s, 1H), 5.81 (s, 1H), 5.00-4.96 (m, 1H), 4.66-4.61 (m, 1H), 4.50-4.44 (m, 1H), 4.40-4.28 (m, 3H), 4.23-4.15 (m, 1H), 3.46 (s, 3H). LCMS R$_{T}$=1.015 min, m/z=420.2 [M+H]$^{+}$.

LCMS (10 to 80% acetonitrile in water+0.03% trifluoacetic acid over 2.0 mins) retention time 1.015 min, ESI+ found [M+H]=420.2.

Example 6

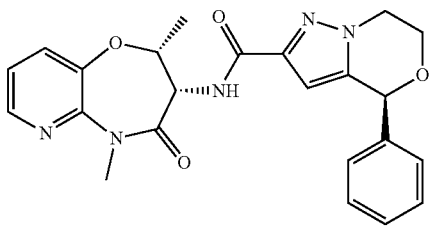 [SMILES: C[C@H]1Oc2cccnc2N(C)C(=O)[C@H]1NC(=O)c1cc2n(n1)CCO[C@H]2c1ccccc1]

(4S)-4-phenyl-N-[(2R,3S)-2,5-dimethyl-4-oxo-2,3-dihydropyrido[3,2-b][1,4]oxazepin-3-yl]-6,7-dihydro-4H-pyrazolo[5,1-c][1,4]oxazine-2-carboxamide

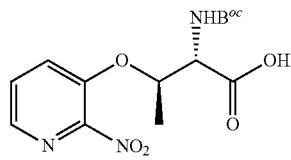 [SMILES: C[C@@H](Oc1cccnc1[N+](=O)[O-])[C@H](NC(=O)OC(C)(C)C)C(=O)O]

Step 1: (2S,3R)-2-((tert-butoxycarbonyl)amino)-3-((2-nitropyridin-3-yl)oxy)butanoic acid Sodium hydride (60%, 9.1 g, 228 mmol) was added to a stirred solution of (2S,3R)-2-(tert-butoxycarbonylamino)-3-hydroxybutanoic acid (25.0 g, 114 mmol) in N,N-dimethylformamide (500 mL). The reaction mixture was stirred at 0° C. for 1 h and 3-fluoro-2-nitropyridine (16.2 g, 114 mmol) was added. After addition, the reaction mixture was stirred at room temperature for another 2 h and then quenched by the addition of aqueous hydrochloride acid (3N, 20 mL). The mixture was adjusted to pH=3-4 with aqueous hydrogen chloride (3N, 20 mL) and extracted with ethyl acetate (3×100 mL). The combined organic layers were dried over anhydrous sodium sulfate and concentrated under reduced pressure. The residue was purified by RP-HPLC (acetonitrile 5-50/0.225% formic acid in water) to afford (2S,3R)-2-((tert-butoxycarbonyl)amino)-3-((2-nitropyridin-3-yl)oxy)butanoic acid (4.1 g, 11%) as a yellow solid.

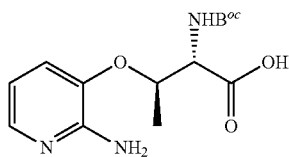

Step 2: (2S,3R)-3-((2-aminopyridin-3-yl)oxy)-2-((tert-butoxycarbonyl)amino)butanoic acid A mixture of (2S,3R)-2-(tert-butoxycarbonylamino)-3-(2-nitropyridin-3-yloxy) butanoic acid (3.2 g, 9.4 mmol) and palladium (10% on carbon, 10 g) in methanol (30 mL) was hydrogenated (40 psi) for 6 h at room temperature and then filtered. The filtrate was concentrated under reduced pressure to afford (2S,3R)-3-((2-aminopyridin-3-yl)oxy)-2-((tert-butoxycarbonyl)amino)butanoic acid (2.9 g, 99%) as a yellow oil and used as without further purification in the next step. LCMS R$_{T}$=0.592 min, m/z=312.2 [M+H]$^{+}$.

LCMS (5 to 95% acetonitrile in water+0.03% trifluoacetic acid over 1.5 mins) retention time 0.592 min, ESI+ found [M+H]=312.2.

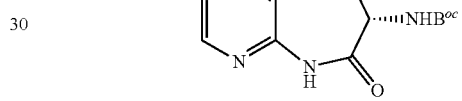

Step 3: tert-butyl ((2R,3S)-2-methyl-4-oxo-2,3,4,5-tetrahydropyrido[3,2-b][1,4]oxazepin-3-yl)carbamate A mixture of (2S,3R)-3-(2-aminopyridin-3-yloxy)-2-(tert-butoxycarbonylamino) butanoic acid (2.9 g, 9.3 mmol), N,N-diisopropylethylamine (4.97 mL, 27.9 mmol) and N,N,N',N'-tetramethyl-0-(7-azabenzotriazol-1-yl)uronium hexafluorophospate (3.9 g, 10.3 mmol) in N,N-dimethylformamide (30 mL) was stirred for 5 h at room temperature and then quenched by the addition of water (20 mL). The mixture was extracted with ethyl acetate (3×100 mL). The combined organic layers were washed with brine, dried over anhydrous sodium sulfate and concentrated under vacuum. The residue was purified by column chromatography (silica gel, 100-200 mesh, 0 to 4% methanol in dichloromethane) to afford tert-butyl ((2R,3S)-2-methyl-4-oxo-2,3,4,5-tetrahydropyrido[3,2-b][1,4]oxazepin-3-yl) carbamate (1.8 g, 66%) as a white solid. LCMS R$_{T}$=1.505 min, m/z=294.2 [M+H]$^{+}$.

LCMS (10 to 80% acetonitrile in water+0.05% ammonium bicarbonate over 2 mins) retention time 1.505 min, ESI+ found [M+H]=294.2

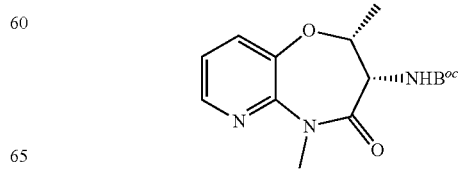

Step 4: tert-butyl ((2R,3S)-2,5-dimethyl-4-oxo-2,3,4,5-tetrahydropyrido[3,2-b] [1,4]oxazepin-3-yl)carbamate Iodomethane (0.17 mL, 2.73 mmol) was added dropwise to a stirred solution of tert-butyl (2R,3S)-2-methyl-4-oxo-2,3,4,5-tetrahydropyrido[3,2-b][1,4]oxazepin-3-yl carbamate (800 mg, 2.73 mmol) and cesium carbonate (888 mg, 2.73 mmol) in N,N-dimethylformamide (15 mL). After addition, the reaction mixture was stirred for 4 h at room temperature and then diluted with water (20 mL). The mixture was then extracted with ethyl acetate (3×100 mL). The combined organic layers were washed with brine, dried over anhydrous sodium sulfate and concentrated under reduced pressure. The residue was purified by column chromatography (silica gel, 100-200 mesh, 0 to 30% ethyl acetate in petroleum ether) to afford tert-butyl ((2R,3S)-2,5-dimethyl-4-oxo-2,3,4,5-tetrahydropyrido[3,2-b][1,4]oxazepin-3-yl)carbamate (500 mg, 60%) as a white solid.

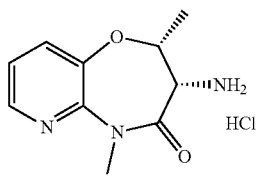

Step 5: (2R,3S)-3-amino-2,5-dimethyl-2,3-dihydropyrido[3,2-b][1,4]oxazepin-4(5H)-one hydrochloride Tert-butyl (2R,3S)-2,5-dimethyl-4-oxo-2,3,4,5-tetrahydropyrido[3,2-b][1,4]oxazepin-3-ylcarbamate (500 mg, 1.63 mmol) was added to a solution of hydrogen chloride in dioxane (4.0 M, 10 mL, 40.0 mmol). The reaction mixture was stirred for 30 min at room temperature and concentrated under reduced pressure to afford crude (2R,3S)-3-amino-2,5-dimethyl-2,3-dihydropyrido[3,2-b][1,4]oxazepin-4(5H)-one hydrochloride (380 mg crude, 96%) as a white solid. LCMS $R_T$=0.399 min, m/z=208.1 [M+H]$^+$.

LCMS (5 to 95% acetonitrile in water+0.03% trifluoacetic acid over 1.5 mins) retention time 0.399 min, ESI+ found [M+H]=208.1.

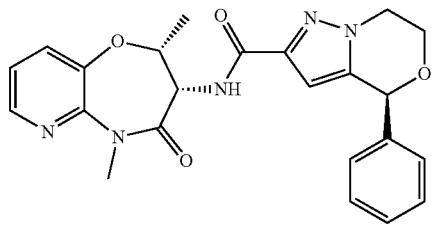 [SMILES: C[C@H]1Oc2cccnc2N(C)C(=O)[C@H]1NC(=O)c1cc2n(n1)CCO[C@H]2c1ccccc1]

Step 6: (4S)-4-phenyl-N-[(2R,3S)-2,5-dimethyl-4-oxo-2,3-dihydropyrido[3,2-b][1,4]oxazepin-3-yl]-6,7-dihydro-4H-pyrazolo [5,1-c][1,4]oxazine-2-carboxamide A mixture of (2R,3S)-3-amino-2,5-dimethyl-2,3-dihydropyrido[3,2-b][1,4]oxazepin-4(5H)-one hydrochloride (80 mg, 0.39 mmol), (4S)-4-phenyl-6,7-dihydro-4H-pyrazolo[5,1-c][1,4]oxazine-2-carboxylic acid (99.0 mg, 0.41 mmol), N,N-diisopropylethylamine (149.7 mg, 1.16 mmol) and 1-[Bis(dimethylamino)methylene]-1H-1,2,3-triazolo[4,5-b]pyridinium 3-oxid hexafluorophosphate (154.1 mg, 0.41 mmol) in N,N-dimethylformamide (1 mL) was stirred at 25° C. for 2 h and concentrated under reduced pressure. The residue was purified by RP-HPLC (acetonitrile 36-66%/0.05% ammonia hydroxide in water) to afford (4S)-4-phenyl-N-[(2R,3S)-2,5-dimethyl-4-oxo-2,3-dihydropyrido[3,2-b][1,4]oxazepin-3-yl]-6,7-dihydro-4H-pyrazolo [5,1-c][1,4]oxazine-2-carboxamide (15 mg, 9%) as a white solid. $^1$H NMR (400 MHz, CDCl$_3$) δ 8.29-8.27 (m, 1H), 7.95-7.90 (m, 1H), 7.53-7.51 (m, 1H), 7.36 (s, 5H), 7.18-7.15 (m, 1H), 6.28 (s, 1H), 5.74 (s, 1H), 5.06-5.02 (m, 2H), 4.39-4.36 (m, 2H), 4.29-4.25 (m, 1H), 4.17-4.13 (m, 1H), 3.53 (s, 3H), 1.45-1.42 (m, 3H). LCMS $R_T$=1.080 min, m/z=434.2 [M+H]$^+$.

LCMS (10 to 80% acetonitrile in water+0.05% ammonium bicarbonate over 2 mins) retention time 1.080 min, ESI+ found [M+H]=434.2.

Example 7

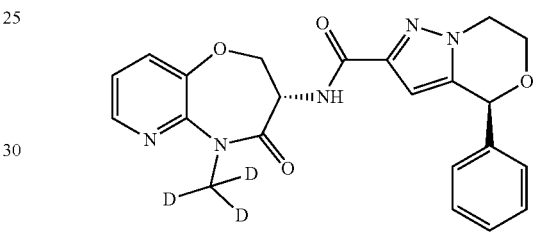

(4S)-4-phenyl-N-[(3S)-4-oxo-5-(trideuteriomethyl)-2,3-dihydropyrido[3,2-b][1,4]oxazepin-3-yl]-6,7-dihydro-4H-pyrazolo[5,1-c][1,4]oxazine-2-carboxamide

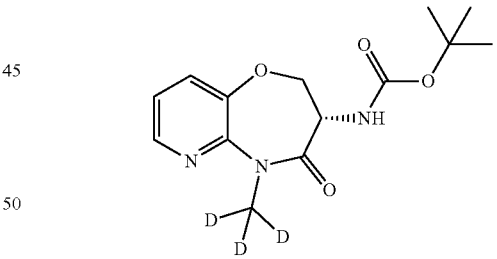

Step 1: tert-butyl N-[(3S)-4-oxo-5-(trideuteriomethyl)-2,3-dihydropyrido[3,2-b][1,4]oxazepin-3-yl] carbamate To a mixture of tert-butyl N-[(3S)-4-oxo-3,5-dihydro-2H-pyrido[3,2-b][1,4]oxazepin-3-yl]carbamate (100 mg, 0.36 mmol) and cesium carbonate (233 mg, 0.72 mmol) in N,N-dimethylformamide (3 mL) was added iodomethane-d$_3$ (78 mg, 0.54 mmol) at 0° C. The mixture was stirred at 0° C. for 1 h, at 15° C. for 3 h and then filtered. The filtrate was concentrated under reduced pressure. The residue was purified by column chromatography (silica gel, 100-200 mesh, 0 to 50% ethyl acetate in petroleum ether) to afford tert-butyl N-[(3S)-4-oxo-5-(trideuteriomethyl)-2,3-dihydropyrido[3,2-b][1,4]oxazepin-3-yl]carbamate (100 mg, 94%) as a white solid. LCMS $R_T$=0.636 min, m/z=297.1 [M+H]⁺.

LCMS (5 to 95% acetonitrile in water+0.03% trifluoacetic acid over 1.5 mins) retention time 0.636 min, ESI+ found [M+H]=297.1

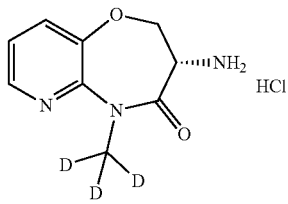 [SMILES: [2H]C([2H])([2H])N1C(=O)[C@@H](N)COc2cccnc21 ; Cl]

Step 2: (3S)-3-amino-5-(trideuteriomethyl)-2,3-dihydropyrido[3,2-b][1,4]oxazepin-4-one hydrochloride A mixture of tert-butyl N-[(3S)-4-oxo-5-(trideuteriomethyl)-2,3-dihydropyrido[3,2-b][1,4]oxazepin-3-yl]carbamate (60 mg, 0.20 mmol) and hydrochloric acid (4 M in ethyl acetate, 10 mL) was stirred at 15° C. for 2 h. The solvent was removed under reduced pressure to afford crude (3S)-3-amino-5-(trideuteriomethyl)-2,3-dihydropyrido[3,2-b][1,4]oxazepin-4-one hydrochloride (35 mg, 74%) as yellow solids, used in the next step without further purification.

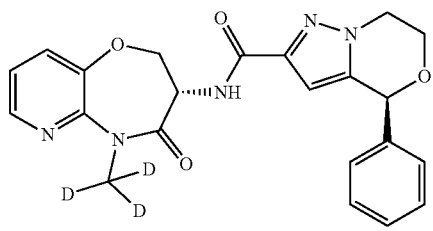 [SMILES: [2H]C([2H])([2H])N1C(=O)[C@@H](NC(=O)c2cc3n(n2)CCO[C@H]3c2ccccc2)COc2cccnc21]

Step 3: (4S)-4-phenyl-N-[(3S)-4-oxo-5-(trideuteriomethyl)-2,3-dihydro pyrido[3,2-b][1,4]oxazepin-3-yl]-6,7-dihydro-4H-pyrazolo[5,1-c][1,4]oxazine-2-carboxamide A mixture of (3S)-3-amino-5-(trideuteriomethyl)-2,3-dihydropyrido[3,2-b][1,4]oxazepin-4-one hydrochloride (35 mg, 0.15 mmol), (4S)-4-phenyl-6,7-dihydro-4H-pyrazolo[5,1-c][1,4]oxazine-2-carboxylic acid (39 mg, 0.16 mmol), 1-[Bis(dimethylamino)methylene]-1H-1,2,3-triazolo[4,5-b]pyridinium 3-oxide hexafluorophosphate (60 mg, 0.16 mmol) and N,N-diisopropylethylamine (58 mg, 0.45 mmol) in N,N-dimethylformamide (1 mL) was stirred at 25° C. for 2 h. The mixture was concentrated under reduced pressure and the residue was purified by RP-HPLC (acetonitrile 35-65%/0.05% ammonium hydroxide in water) to afford crude product, which was further purified by preparative TLC (50% ethyl acetate in petroleum ether, $R_f$=0.2) to afford (4S)—N-[(3S)-4-oxo-5-(trideuteriomethyl)-2,3-dihydropyrido[3,2-b][1,4]oxazepin-3-yl]-4-phenyl-6,7-dihydro-4H-pyrazolo[5,1-c][1,4]oxazine-2-carboxamide (11.6 mg, 18%) as white solid. ¹HNMR (400 MHz, CDCl₃) δ 8.27-8.32 (m, 1H), 7.85-7.80 (m, 1H), 7.54-7.50 (m, 1H), 7.38-7.31 (m, 5H), 7.19-7.13 (m, 1H), 6.29-6.24 (m, 1H), 5.74-5.70 (m, 1H), 5.08-5.01 (m, 1H), 4.82-4.75 (m, 1H), 4.39-4.32 (m, 2H), 4.31-4.22 (m, 2H), 4.16-4.10 (m, 1H). LCMS $R_T$=0.885 min, m/z=423.0 [M+H]⁺.

LCMS (5 to 95% acetonitrile in water+0.03% trifluoacetic acid over 1.5 mins) retention time 0.885 min, ESI+ found [M+H]=423.0.

Example 8

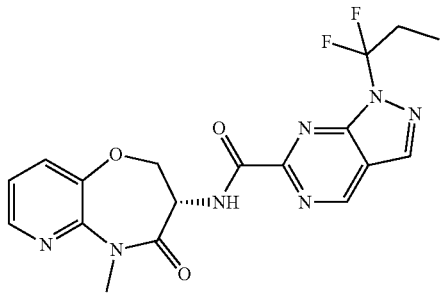 [SMILES: CCC(F)(F)n1ncc2cnc(C(=O)N[C@H]3COc4cccnc4N(C)C3=O)nc21]

1-(1,1-difluoropropyl)-N-[(3S)-5-methyl-4-oxo-2,3-dihydropyrido[3,2-b][1,4]oxazepin-3-yl]pyrazolo[3,4-d]pyrimidine-6-carboxamide

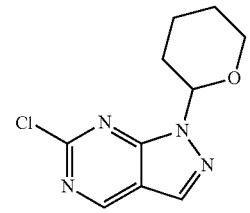 [SMILES: Clc1ncc2cnn(C3CCCCO3)c2n1]

Step 1: 6-chloro-1-tetrahydropyran-2-yl-pyrazolo[3, 4-d]pyrimidine

A mixture of 6-chloro-1H-pyrazolo[3,4-d]pyrimidine (1.25 g, 8.09 mmol), pyridinium p-toluene sulfonate (203 mg, 0.81 mmol) and 3,4-dihydro-2h-pyran (1.36 g, 16.17 mmol) in dichloromethane (25 mL) was heated at reflux for 6 h and concentrated under reduced pressure. The residue was purified by column chromatography (silica gel, 100-200 mesh, 0 to 40% ethyl acetate in petroleum ether) to afford 6-chloro-1-tetrahydropyran-2-yl-pyrazolo [3,4-d]pyrimidine (1.8 g, 93%) as a white solid. ¹H NMR (400 MHz, CDCl₃) δ 9.10-8.99 (m, 1H), 8.26-8.14 (m, 1H), 6.13-5.98 (m, 1H), 4.21-4.09 (m, 1H), 3.91-3.76 (m, 1H), 2.67-2.48 (m, 1H), 2.59-2.48 (m, 1H), 2.21-2.09 (m, 1H), 2.00-1.91 (m, 1H), 1.86-1.75 (m, 2H), 1.70-1.60 (m, 1H).

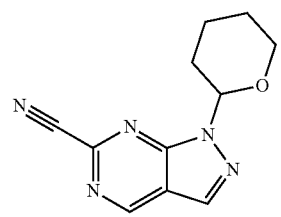 [SMILES: N#Cc1ncc2cnn(C3CCCCO3)c2n1]

Step 2: 1-tetrahydropyran-2-ylpyrazolo[3,4-d]pyrimidine-6-carbonitrile

To a solution of 6-chloro-1-tetrahydropyran-2-yl-pyrazolo[3,4-d]pyrimidine (1.80 g, 7.54 mmol) in water (25 mL) and 1,4-dioxane (25 mL) was added di-tert-butyl(2',4',6'-triisopropyl-[1,1'-biphenyl]-2-yl)phosphine (320 mg, 0.75 mmol), potassium hexacyanoferrate(II) trihydrate (1.59 g, 3.77 mmol), [2-(2-aminophenyl)phenyl]-methylsulfonyloxy-palladium ditert-butyl-[2-(2,4,6-triiso propylphenyl)phenyl]phosphane (599 mg, 0.75 mmol) and palladium(II) acetate (92 mg, 0.94 mmol). The reaction was stirred at 100° C. for 6 h under nitrogen atmosphere and filtered through a short pad of celite. The filtrate was concentrated under reduced pressure and the residue was purified by column chromatography (silica gel, 100-200 mesh, 0 to 40% ethyl acetate in petroleum ether) to afford 1-tetrahydropyran-2-ylpyrazolo [3,4-d]pyrimidine-6-carbonitrile (1.15 g, 66.5%) as a light yellow solid, used in the next step without further purification.

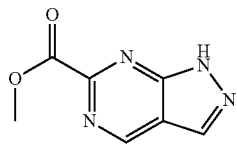

Step 3: methyl 1H-pyrazolo[3,4-d]pyrimidine-6-carboxylate

A mixture of 1-tetrahydropyran-2-ylpyrazolo [3,4-d]pyrimidine-6-carbonitrile (1250 mg, 5.45 mmol) and hydrochloric acid (4 M in methanol, 15 mL) was stirred at 40° C. for 3 h and concentrated under reduced pressure to give crude methyl 1H-pyrazolo [3,4-d]pyrimidine-6-carboxylate (970 mg, 99%) as a white solid, used in the next step without further purification.

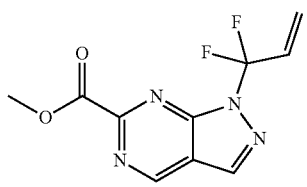 [SMILES: C=CC(F)(F)n1ncc2cnc(C(=O)OC)nc21]

Step 4: methyl 1H-pyrazolo[3,4-d]pyrimidine-6-carboxylate

A mixture of methyl 1H-pyrazolo[3,4-d]pyrimidine-6-carboxylate (500 mg, 2.81 mmol), triethylamine (568 mg, 5.61 mmol) and 3-bromo-3,3-difluoropropene (660 mg, 4.21 mmol) in N,N-dimethylformamide (6 mL) was stirred at 20° C. for 2 h and filtered through a short pad of celite. The filtrate was concentrated under reduced pressure and the residue was purified by column chromatography (silica gel, 100-200 mesh, 0 to 40% ethyl acetate in petroleum ether) to afford methyl 1-(1,1-difluoroallyl)pyrazolo[3,4-d]pyrimidine-6-carboxylate (100 mg, 14%) as a white solid. $^1$H NMR (400 MHz, CDCl$_3$) δ 9.40 (s, 1H), 8.35 (s, 1H), 6.79-6.66 (m, 1H), 6.13-6.06 (m, 1H), 5.87 (d, J=11.2 Hz, 1H), 4.14-4.04 (m, 3H). LCMS R$_T$=1.714 min, m/z=255.1 [M+H]$^+$.

LCMS (0 to 60% acetonitrile in water+0.05% ammonium hydroxide over 3 mins) retention time 1.714 min, ESI+ found [M+H]=255.1.

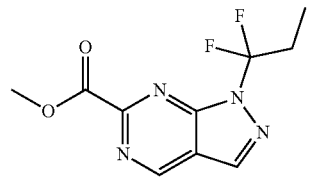 [SMILES: CCC(F)(F)n1ncc2cnc(C(=O)OC)nc21]

Step 5: methyl 1-(1,1-difluoropropyl)pyrazolo[3,4-d]pyrimidine-6-carboxylate

A mixture of methyl 1-(1,1-difluoroallyl)pyrazolo[3,4-d]pyrimidine-6-carboxylate (82 mg, 0.32 mmol) and palladium (10% on carbon, 7 mg) in methanol (10 mL) was hydrogenated (15 psi) at 0° C. for 8 min and filtered. The filtrate was concentrated under reduced pressure to afford crude methyl 1-(1,1-difluoropropyl)pyrazolo[3,4-d] pyrimidine-6-carboxylate (82 mg, 99%) as light yellow oil. The resultant crude was used in the next step without further purification.

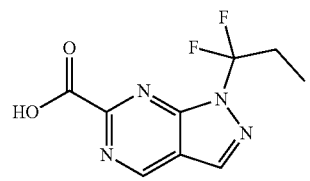 [SMILES: CCC(F)(F)n1ncc2cnc(C(=O)O)nc21]

Step 6: 1-(1,1-difluoropropyl)-1H-pyrazolo[3,4-d]pyrimidine-6-carboxylic acid

To a cooled solution of methyl 1-(1,1-difluoropropyl)pyrazolo[3,4-d] pyrimidine-6-carboxylate (82 mg, 0.32 mmol) in water (1 mL)/tetrahydrofuran (2 mL) was added lithium hydroxide monohydrate (20 mg, 0.48 mmol) at 0° C. The mixture was stirred at 0° C. for 2 h and concentrated under reduced pressure. The residue was diluted with water (10 mL), and adjusted to pH=4 by addition of aqueous hydrochloric acid (1 M) at 0° C. The resulting mixture was extracted with ethyl acetate (2×20 mL). The combined organic layers were dried and concentrated under reduced pressure to afford crude 1-(1,1-difluoropropyl)pyrazolo[3,4-d] pyrimidine-6-carboxylic acid (70 mg, 90%) as a white solid, used in the next step without further purification.

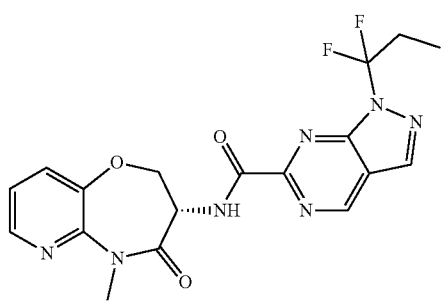 [SMILES: CCC(F)(F)n1ncc2cnc(C(=O)N[C@H]3COc4cccnc4N(C)C3=O)nc21]

Step 7: 1-(1,1-difluoropropyl)-N-[(3S)-5-methyl-4-oxo-2,3-dihydropyrido[3,2-b][1,4]oxazepin-3-yl]pyrazolo[3,4-d]pyrimidine-6-carboxamide A mixture of (3S)-3-amino-5-methyl-2,3-dihydropyrido[3,2-b][1,4]oxazepin-4-one (16 mg, 0.08 mmol), 1-(1,1-difluoropropyl)pyrazolo[3,4-d]pyrimidine-6-carboxylic acid (20 mg, 0.08 mmol), N,N-diisopropylethylamine (32 mg, 0.25 mmol) and 1-[Bis(dimethylamino)methylene]-1H-1,2,3-triazolo[4,5-b]pyridinium 3-oxide hexafluorophosphate (33 mg, 0.09 mmol) in N,N-dimethylformamide (2 mL) was stirred at 20° C. for 4 h and concentrated under reduced pressure. The residue was purified by RP-HPLC (acetonitrile 29-59%/0.04% $NH_3H_2O$+10 mM $NH_4HCO_3$ in water) to afford 1-(1,1-difluoropropyl)-N-[(3S)-5-methyl-4-oxo-2,3-dihydropyrido[3,2-b][1,4]oxazepin-3-yl]pyrazolo[3,4-d]pyrimidine-6-carboxamide (6.9 mg, 20%) as a white solid. $^1$H NMR (400 MHz, $CDCl_3$) δ 9.38 (s, 1H), 9.10 (d, J=5.6 Hz, 1H), 8.36-8.30 (m, 2H), 7.59-7.52 (m, 1H), 7.24-7.20 (m, 1H), 5.16-5.07 (m, 1H), 5.00-4.90 (m, 1H), 4.44-4.34 (m, 1H), 3.57 (s, 3H), 2.95-2.85 (m, 2H), 1.24 (t, J=7.6 Hz, 3H). LCMS $R_T$=0.865 min, m/z=418.1 [M+H]$^+$.

LCMS (5 to 95% acetonitrile in water+0.03% trifluoacetic acid over 1.5 mins) retention time 0.865 min, ESI+ found [M+H]=418.1.

Example 9

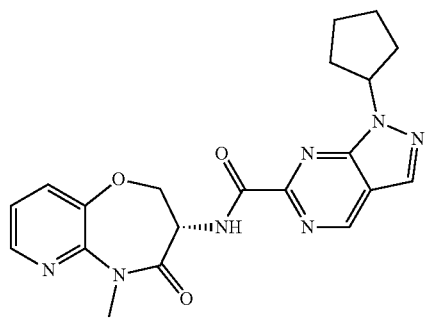 [SMILES: CN1C(=O)[C@@H](NC(=O)c2ncc3cnn(C4CCCC4)c3n2)COc2cccnc21]

1-cyclopentyl-N-[(3S)-5-methyl-4-oxo-2,3-dihydropyrido[3,2-b][1,4]oxazepin-3-yl]pyrazolo [3,4-d]pyrimidine-6-carboxamide A mixture of (3S)-3-amino-5-methyl-2,3-dihydropyrido[3,2-b][1,4]oxazepin-4-one hydrochloride (79 mg, 0.34 mmol), 1-cyclopentylpyrazolo[3,4-d]pyrimidine-6-carboxylic acid (84 mg, 0.36 mmol), N,N-diisopropylethylamine (0.17 mL, 1.03 mmol) and 1-[Bis(dimethylamino)methylene]-1H-1,2,3-triazolo[4,5-b]pyridinium 3-oxide hexafluorophosphate (137 mg, 0.36 mmol) in N,N-dimethylformamide (1 mL) was stirred at 25° C. for 2 h and concentrated under reduced pressure. The residue was purified by RP-HPLC (acetonitrile 35-65%/0.05% ammonia hydroxide in water) to afford 1-cyclopentyl-N-[(3S)-5-methyl-4-oxo-2,3-dihydropyrido[3,2-b][1,4] oxazepin-3-yl]pyrazolo[3,4-d]pyrimidine-6-carboxamide (11.6 mg, 8%) as a white solid. NMR (400 MHz, $CDCl_3$) δ 9.26 (s, 1H), 9.17-9.02 (m, 1H), 8.34-8.26 (m, 1H), 8.24 (s, 1H), 7.58-7.47 (m, 1H), 7.23-7.12 (m, 1H), 5.59-5.54 (m, 1H), 5.15-5.07 (m, 1H), 4.95-4.87 (m, 1H), 4.39-4.31 (m, 1H), 3.58 (s, 3H), 2.24-2.18 (m, 2H), 2.17-2.09 (m, 2H), 2.07-1.95 (m, 2H), 1.88-1.72 (m, 2H). LCMS $R_T$=1.691 min, m/z=408.2 [M+H]$^+$.

LCMS (10 to 80% acetonitrile in water+0.05% ammonium hydroxide over 3 mins) retention time 1.691 min, ESI+ found [M+H]=408.2.

Example 10

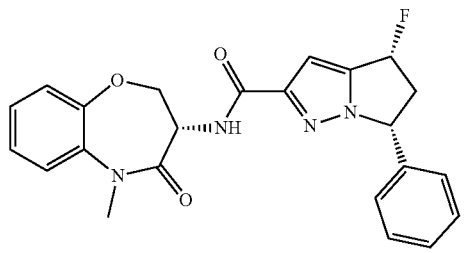 [SMILES: CN1C(=O)[C@@H](NC(=O)c2cc3n(n2)[C@@H](c2ccccc2)C[C@H]3F)COc2ccccc21]

(4R,6R)-4-fluoro-6-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide

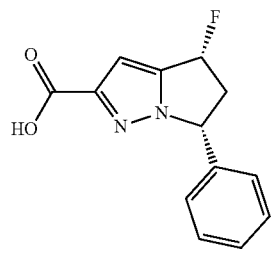 [SMILES: O=C(O)c1cc2n(n1)[C@@H](c1ccccc1)C[C@H]2F]

Step 1: (4R,6R)-4-fluoro-6-phenyl-5,6-dihydro-4H-pyrrolo[1,2-b]pyrazole-2-carboxylic acid A mixture of ethyl (4R,6R)-4-fluoro-6-phenyl-5,6-dihydro-4H-pyrrolo[1,2-b]pyrazole-2-carboxylate (140 mg, 0.51 mmol) and lithium hydroxide monohydrate (107 mg, 2.55 mmol) in tetrahydrofuran (5 mL), methanol (1 mL) and water (1 mL) was stirred at 20° C. for 16 h. The mixture was adjusted to pH=5 by addition of aqueous hydrochloric acid (1 M) and concentrated under reduced pressure. The residue was added a mixture of 10% methanol in dichloromethane (20 mL) and filtered. The filtrate was concentrated under reduced pressure to give the crude (4R,6R)-4-fluoro-6-phenyl-5,6-dihydro-4H-pyrrolo[1,2-b]pyrazole-2-carboxylic acid (120 mg, 96%) as a white solid. This crude was used directly for next step.

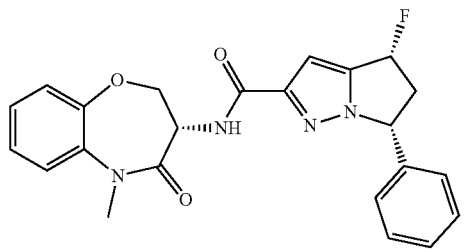 [SMILES: CN1C(=O)[C@@H](NC(=O)c2cc3n(n2)[C@@H](c2ccccc2)C[C@H]3F)COc2ccccc21]

Step 2 (4R,6R)-4-fluoro-6-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide A mixture of (4R,6R)-4-fluoro-6-phenyl-5,6-dihydro-4H-pyrrolo[1,2-b]pyrazole-2-carboxylic acid (55.0 mg, 0.22 mmol), (3S)-3-amino-5-methyl-2,3-dihydro-1,5-benzoxazepin-4-one (42.9 mg, 0.22 mmol), 1-hydroxybenzotriazole (6.0 mg, 0.04 mmol) and 1-(3-dimethylaminopropyl)-3-ethylcarbodiimidehydrochloride (64.2 mg, 0.34 mmol) in N,N-dimethylformamide (3 mL) was stirred at 25° C. for 16 h and concentrated under reduced pressure. The residue was purified by RP-HPLC (acetonitrile 36-66/0.05% ammonia hydroxide in water) to afford (4R,6R)-4-fluoro-6-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide (50 mg, 53%) as a white solid. NMR (400 MHz, CDCl$_3$) δ 7.70-7.66 (m, 1H), 7.40-7.19 (m, 8H), 6.86 (s, 1H), 6.10-5.83 (m, 1H), 5.48-5.42 (m, 1H), 5.15-4.97 (m, 1H), 4.69-4.64 (m, 1H), 4.25-4.19 (m, 1H), 3.58-3.29 (m, 4H), 2.92-2.69 (m, 1H). LCMS RT=0.915 min, m/z=421.1 [M+H]$^+$.

LCMS (5 to 95% acetonitrile in water+0.1% formic acid over 1.5 mins) retention time 0.915 min, ESI+ found [M+H]=421.1.

Example 11

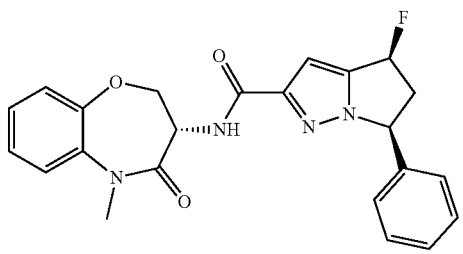 [SMILES: CN1C(=O)[C@@H](NC(=O)c2cc3n(n2)[C@H](c2ccccc2)C[C@@H]3F)COc2ccccc21]

(4S,6S)-4-fluoro-6-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide A mixture of (4S,6S)-4-fluoro-6-phenyl-5,6-dihydro-4H-pyrrolo[1,2-b]pyrazole-2-carboxylic acid (45.0 mg, 0.18 mmol), (3S)-3-amino-5-methyl-2,3-dihydro-1,5-benzoxazepin-4-one (35.1 mg, 0.18 mmol), 1-hydroxybenzotriazole (4.9 mg, 0.04 mmol) and 1-(3-dimethylaminopropyl)-3-ethylcarbodiimidehydrochloride (52.6 mg, 0.27 mmol) in N,N-dimethylformamide (3 mL) was stirred at 25° C. for 16 h and concentrated under reduced pressure. The residue was purified by RP-HPLC (acetonitrile 50-80/0.225% formic acid in water) to afford (4S,6S)-4-fluoro-6-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide (27 mg, 34%) as a white solid. $^1$H NMR (400 MHz, CDCl$_3$) δ 7.69-7.66 (m, 1H), 7.37-7.33 (m, 3H), 7.24-7.13 (m, 5H), 6.87 (s, 1H), 6.07-5.86 (m, 1H), 5.42 (s, 1H), 5.07-5.00 (m, 1H), 4.76-4.70 (m, 1H), 4.26-4.18 (m, 1H), 3.57-3.30 (m, 4H), 2.93-2.72 (m, 1H). LCMS R$_T$=0.895 min, m/z=421.1 [M+H]$^+_o$ LCMS (5 to 95% acetonitrile in water+0.1% formic acid over 1.5 mins) retention time 0.895 min, ESI+ found [M+H]=421.1.

Example 12

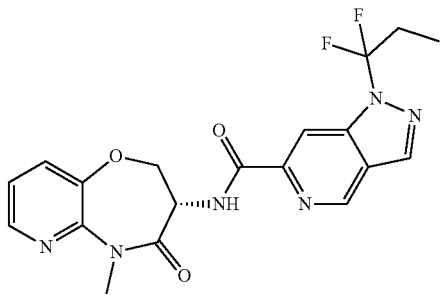 [SMILES: CCC(F)(F)n1ncc2cnc(C(=O)N[C@H]3COc4cccnc4N(C)C3=O)cc21]

1-(1,1-difluoropropyl)-N-[(3S)-5-methyl-4-oxo-2,3-dihydropyrido[3,2-b][1,4]oxazepin-3-yl]pyrazolo[4,3-c]pyridine-6-carboxamide A mixture of (3S)-3-amino-5-methyl-2,3-dihydropyrido[3,2-b][1,4]oxazepin-4-one (15 mg, 0.08 mmol), 1-(1,1-difluoropropyl)pyrazolo[4,3-c]pyridine-6-carboxylic acid (19 mg, 0.08 mmol) and N,N-diisopropylethylamine (30 mg, 0.23 mmol) and 1-[Bis(dimethylamino)methylene]-1H-1,2,3-triazolo[4,5-b]pyridinium 3-oxid hexafluorophosphate (31 mg, 0.08 mmol) in N,N-dimethylformamide (1 mL) was was stirred at 25° C. for 2 h. The reaction mixture was concentrated under reduced pressure and the residue was purified by RP-HPLC (45%-75% acetonitrile/water (0.05% ammonia hydroxide)) to afford 1-(1,1-difluoropropyl)-N-[(3S)-5-methyl-4-oxo-2,3-dihydropyrido[3,2-b][1,4]oxazepin-3-yl]pyrazolo[4,3-c]pyridine-6-carboxamide (3 mg, 9%) as a white solid. $^1$H NMR (400 MHz, CDCl$_3$) δ 9.18-9.14 (m, 1H), 9.09 (d, J=0.8 Hz, 1H), 8.52 (s, 1H), 8.34-8.31 (m, 1H), 8.27 (s, 1H), 7.62-7.47 (m, 1H), 7.24-7.18 (m, 1H), 5.15-5.06 (m, 1H) 4.90-4.83 (m, 1H), 4.48-4.30 (m, 1H), 3.56 (s, 3H), 2.83-2.66 (m, 2H), 1.17 (t, J=7.6 Hz, 3H). LCMS R$_T$=1.072 min, m/z=417.2 [M+H]$^+$.

LCMS (10 to 80% acetonitrile in water+0.03% trifluoacetic acid over 2.0 mins) retention time 1.072 min, ESI+ found [M+H]=417.2.

RIP1 Kinase Inhibition Assays (Biochemical Assay)

The compounds of the present invention were tested for their capacity to inhibit RIP1K activity as described below.

Enzyme assay: The ability of the receptor interacting protein kinase (RIPK1) to catalyze the hydrolysis of adenosine-5'-triphosphate (ATP) is monitored using the Transcreener ADP (adenosine-5'-diphosphate) assay (BellBrook Labs). Purified human RIP1 kinase domain (2-375) (50 nM) derived from a baculovirus-infected insect cell expression system is incubated with test compounds for 2 hours in 50 mM Hepes buffer (pH 7.5) containing 30 mM MgCl$_2$, 1 mM dithiothreitol, 50 uM ATP, 0.002% Brij-35, and 0.5% dimethyl sulfoxide (DMSO). Reactions are quenched by the addition of 1× Bell Brooks Stop buffer B (20 mM Hepes (ph7.5), 40 mM ethylenediaminetetraacetic acid and 0.02% Brij-35) containing an additional 12 mM EDTA and 55 ug/mL ADP2 antibody and 4 nM ADP-AlexaFluor® 633 tracer. The tracer bound to the antibody is displaced by the ADP generated during the RIP1K reaction, which causes a decrease in fluorescence polarization that is measured by laser excitation at 633 nm with a FP microplate reader M1000. Fractional activity was plotted against test article concentration. Using Genedata Screener software (Genedata; Basel, Switzerland), the data were fit to the tight-binding apparent inhibition constant ($K_i^{app}$) Morrison equation [Williams, J. W. and Morrison, J. F. (1979) The kinetics of reversible tight-binding inhibition. *Methods Enzymol* 63: 437-67]. The following equation was used to calculate fractional activity and $K_i^{app}$:

Fractional activity =

$$\frac{v_i}{v_o} = 1 - \frac{([E]_T + [I]_T + K_i^{app}) - \sqrt{([E]_T + [I]_T + K_i^{app})^2 - 4[E]_T[I]_T}}{2[E]_T}$$

where $[E]_T$ and $[I]_T$ are the total concentrations of active enzyme and test article, respectively.

Exemplary compounds of the present invention are provided in Table 1 along with their physiochemical characterization and in vitro RIP1 kinase inhibitory activity data. "Method" in the first column of each table refers to the synthetic method(s) used to prepare each compound as shown in the Examples above. In certain examples, chiral column retention times (min) are provided for certain stereoisomers. Unless otherwise specified, the stereochemistry shown in each structure represents relative configuration of a single stereoisomer, and absolute configuration (i.e., "R" and/or "S") is arbitrarily assigned. In some embodiments, where the Method is described to include the separation of stereoisomers, a single stereoisomer of a compound of Table 1 is provided.

TABLE 1

| Example # Ki (uM) | Structure | Stereo | | MS (m/z) R.T. |
|---|---|---|---|---|
| Example 1 0.0052 | | Single Unknown Stereoisomer | (4S,6S)-4-fluoro-6-phenyl-N-[(3S)-5-methyl-4-oxo-2,3-dihydropyrido[3,2-b][1,4]oxazepin-3-yl]-5,6-dihydro-4H-pyrrolo[1,2-b]pyrazole-2-carboxamide | 422.1 0.863 min |
| Example 2 0.014 | | Single Known Stereoisomer | 1-isopropyl-N-[(3S)-5-methyl-4-oxo-2,3-dihydropyrido[3,2-b][1,4]oxazepin-3-yl]pyrazolo[3,4-d]pyrimidine-6-carboxamide | 382.2 0.958 min |
| Example 3 0.024 | | Single Unknown Stereoisomer | (4S)-4-(2-fluorophenyl)-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide | 438.1 0.844 min |
| Example 4 0.950 | | Single Unknown Stereoisomer | (R)-4-(2-fluorophenyl)-N-((S)-5-methyl-4-oxo-2,3,4,5-tetrahydropyrido[3,2-b][1,4]oxazepin-3-yl)-6,7-dihydro-4H-pyrazolo[5,1-c][1,4]oxazine-2-carboxamide | 438.1 0.840 min |

TABLE 1-continued

| Example # Ki (uM) | Structure | Stereo | | MS (m/z) R.T. |
|---|---|---|---|---|
| Example 5 0.019 | 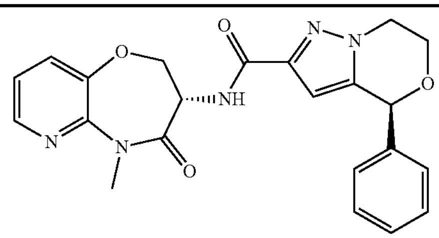 | Single Unknown Stereoisomer | (4S)-4-phenyl-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide | 420.2 1.105 min |
| Example 6 0.007 | 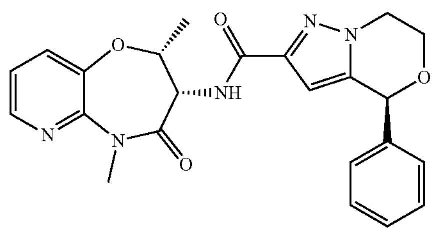 [SMILES: C[C@H]1Oc2cccnc2N(C)C(=O)[C@H]1NC(=O)c1cc2n(n1)CCO[C@H]2c1ccccc1] | Single Known Stereoisomer | (4S)-4-phenyl-N-[(2R,3S)-2,5-dimethyl-4-oxo-2,3-dihydropyrido[3,2-b][1,4]oxazepin-3-yl]-6,7-dihydro-4H-pyrazolo[5,1-c][1,4]oxazine-2-carboxamide | 420.2 1.015 min |
| Example 7 0.028 | 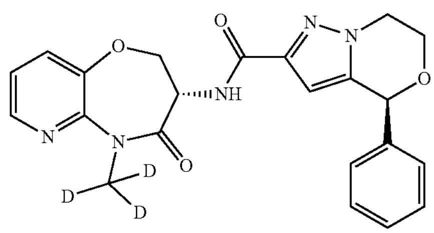 [SMILES: [2H]C([2H])([2H])N1C(=O)[C@@H](NC(=O)c2cc3n(n2)CCO[C@H]3c2ccccc2)COc2cccnc21] | Single Known Stereoisomer | (4S)-4-phenyl-N-[(3S)-4-oxo-5-(trideuteriomethyl)-2,3-dihydropyrido[3,2-b][1,4]oxazepin-3-yl]-6,7-dihydro-4H-pyrazolo[5,1-c][1,4]oxazine-2-carboxamide | 423.0 0.885 min |
| Example 8 0.018 | 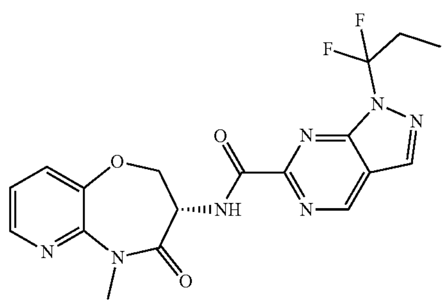 | Single Known Stereoisomer | 1-(1,1-difluoropropyl)-N-[(3S)-5-methyl-4-oxo-2,3-dihydropyrido[3,2-b][1,4]oxazepin-3-yl]pyrazolo[3,4-d]pyrimidine-6-carboxamide | 418.1 0.865 min |
| Example 9 0.011 | 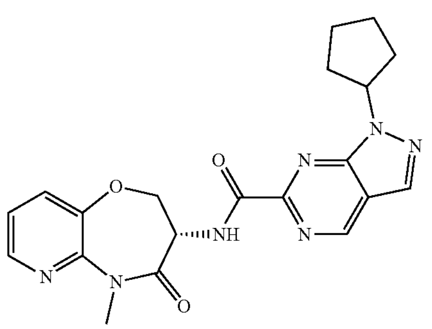 [SMILES: CN1C(=O)[C@@H](NC(=O)c2ncc3cnn(C4CCCC4)c3n2)COc2cccnc21] | Single Known Stereoisomer | 1-cyclopentyl-N-[(3S)-5-methyl-4-oxo-2,3-dihydropyrido[3,2-b][1,4]oxazepin-3-yl]pyrazolo[3,4-d]pyrimidine-6-carboxamide | 408.2 1.691 min |
| Example 10 5.4 | 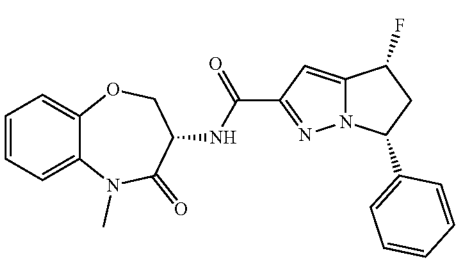 [SMILES: CN1C(=O)[C@@H](NC(=O)c2cc3n(n2)[C@@H](c2ccccc2)C[C@H]3F)COc2ccccc21] | Single Unknown Stereoisomer | (4R,6R)-4-fluoro-6-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide | 421.1 0.915 min |

TABLE 1-continued

| Example # Ki (uM) | Structure | Stereo | | MS (m/z) R.T. |
|---|---|---|---|---|
| Example 11 0.0044 | 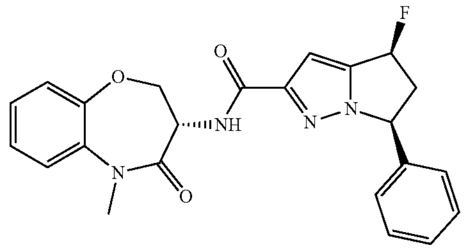 [SMILES: CN1C(=O)[C@@H](NC(=O)c2cc3n(n2)[C@H](c2ccccc2)C[C@@H]3F)COc2ccccc21] | Single Unknown Stereoisomer | (4S,6S)-4-fluoro-6-phenyl-N-[(3S)-5-methyl-4-oxo-2,3-dihydro-1,5-benzoxazepin-3-yl]-5,6-dihydro-4H-pyrrolo[1,2-b]pyrazole-2-carboxamide | 421.1 0.895 min, |
| Example 12 0.005 | 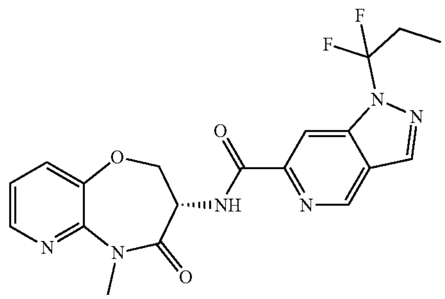 [SMILES: CCC(F)(F)n1ncc2cnc(C(=O)N[C@H]3COc4cccnc4N(C)C3=O)cc21] | Single Known Stereoisomer | 1-(1,1-difluoropropyl)-N-[(3S)-5-methyl-4-oxo-2,3-dihydropyrido[3,2-b][1,4]oxazepin-3-yl]pyrazolo[4,3-c]pyridine-6-carboxamide | 417.2 1.072 min, |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

I claim:
1. A compound of formula I:

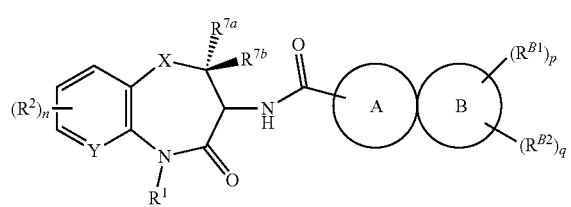

or a pharmaceutically acceptable salt thereof, wherein:
$R^1$ is selected from the group consisting of hydrogen, $C_1$-$C_4$ alkyl, and $CD_3$;
each $R^1$ is independently selected from the group consisting of hydrogen, deutero, halogen, cyano, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, cyano, phenyl, benzyl, $CH_2$—($C_1$-$C_6$ cycloalkyl), $CH_2CH_2$—($C_3$-$C_6$ cycloalkyl), $C_4$-$C_6$ heterocyclyl, $C_5$-$C_6$ heteroaryl, $CH_2$—($C_4$-$C_6$ heterocyclyl), $CH_2CH_2$—($C_4$-$C_6$ heterocyclyl), $CH_2$—($C_5$-$C_6$ heteroaryl), and $CH_2CH_2$—($C_5$-$C_6$ heteroaryl);

n is 0, 1 or 2;
X is selected from the group consisting of O, S, S(O), $SO_2$, $CH_2$, $CH(CH_3)$, $C(CH)_2$, $CF_2$ and $CHCF_3$;
Y is N;
the A ring and the B ring are fused to form a polycyclic ring system, wherein:
the A ring is either:
(i) a 5 membered heteroaromatic ring having as its only heteroatoms, either (a) two or three nitrogen atoms, (b) one nitrogen atom and one oxygen atom, or (c) one nitrogen atom and one sulfur atom; or
(ii) a 6 membered heteroaromatic ring having as its only heteroatoms 1 to 3 nitrogen atoms;
wherein the A ring is optionally substituted at a carbon atom by one substituent selected from the group consisting of fluoro, chloro, methyl, and trifluoromethyl; and
the B ring is a 5 to 7 membered carbocyclic ring, a 5 to 7 membered heterocyclic ring, or a 5 to 6 membered heteroaryl ring, wherein the heterocyclic or heteroaryl ring has 1 to 3 heteroatoms selected from the group consisting of nitrogen, oxygen, and sulfur;
p is 1 or 2, and q is 0 or 1; or p is 0, and q is 1;
each $R^{B1}$ is independently selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, and cyano; wherein two $C_1$-$C_6$ alkyl substituents may together form a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom;
$R^{B2}$ is selected from the group consisting of $C_1$-$C_6$ alkyl, $C_1$-$C_6$ haloalkyl, $C_3$-$C_6$ cycloalkyl, $C_3$-$C_6$ alkoxy, $C_1$-$C_6$ haloalkoxy, $C_1$-$C_6$ thioalkyl, $C_1$-$C_6$ alkyl-$N(R^N)_2$, phenyl, benzyl, $CH_2$—($C_3$-$C_6$ cycloalkyl), CH$_2$CH$_2$—(C$_3$-C$_6$ cycloalkyl), CH$_2$-(4 to 6 membered heterocyclyl), CH$_2$CH$_2$-(4 to 6 membered heterocyclyl), 5 to 6 membered heteroaryl, and CH$_2$-(5 to 6 membered heteroaryl); wherein when R$^{B2}$ is phenyl or benzyl the phenyl ring is optionally substituted by 1 to 3 substituents selected from the group consisting of halogen, C$_1$-C$_4$ alkyl, C$_1$-C$_4$ haloalkyl, C$_1$-C$_4$ alkoxy, C$_1$-C$_4$ haloalkoxy, and cyano;

R$^{7a}$ and R$^{7b}$ are each independently selected from the group consisting of H, halogen, and C$_1$-C$_6$ alkyl; or R$^{7a}$ and R$^{7b}$ may together with the carbon atom to which they are both attached form cyclopropyl; and each R$^N$ is independently selected from the group consisting of C$_1$-C$_6$ alkyl, C$_3$-C$_6$ cycloalkyl, C$_1$-C$_6$ alkoxy, and C$_1$-C$_6$ haloalkyl; or two R$^N$ together with the nitrogen atom to which they are both attached form a 4-6 membered heterocyclic ring;

provided that if n is 2, only one R$^2$ may be phenyl, benzyl, CH$_2$—(C$_3$-C$_6$ cycloalkyl), CH$_2$CH$_2$—(C$_3$-C$_6$ cycloalkyl), C$_4$-C$_6$ heterocyclyl, C$_5$-C$_6$ heteroaryl, CH$_2$—(C$_4$-C$_6$ heterocyclyl), CH$_2$CH$_2$—(C$_4$-C$_6$ heterocyclyl), CH$_2$—(C$_5$-C$_6$ heteroaryl), or CH$_2$CH$_2$—(C$_5$-C$_6$ heteroaryl).

2. The compound of claim 1, or a pharmaceutically acceptable salt thereof, wherein the A ring and the B ring together are selected from the group consisting of:

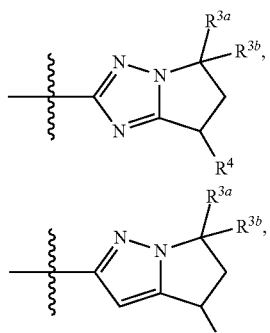
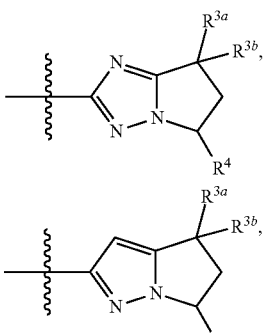
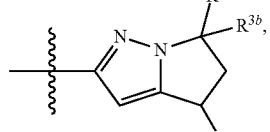
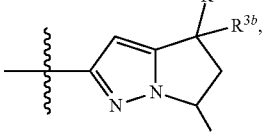
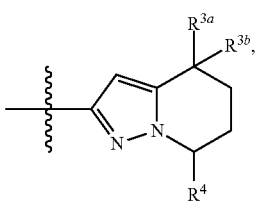
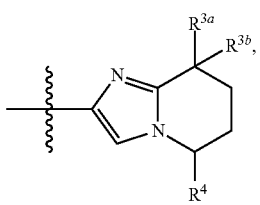
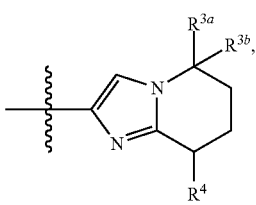
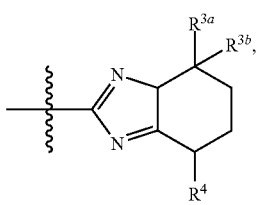
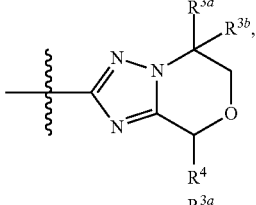
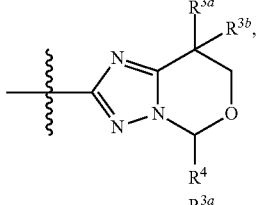
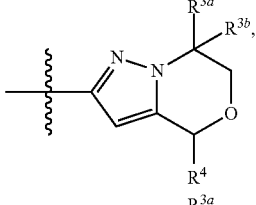
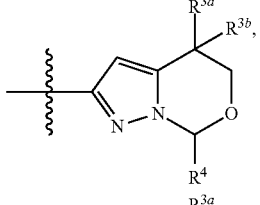
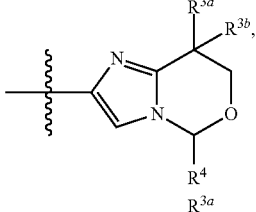
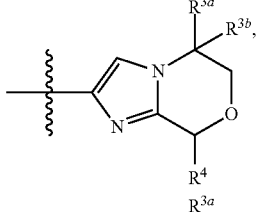
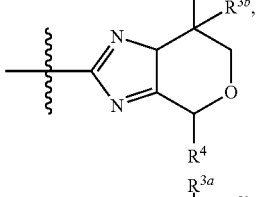
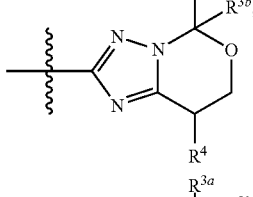
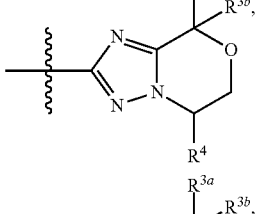
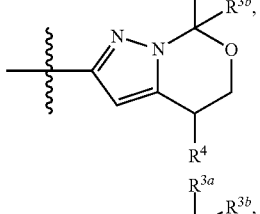
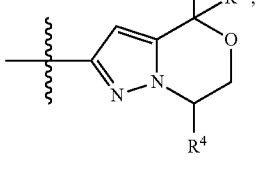
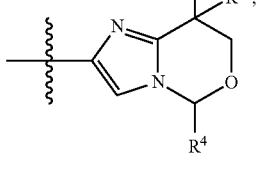

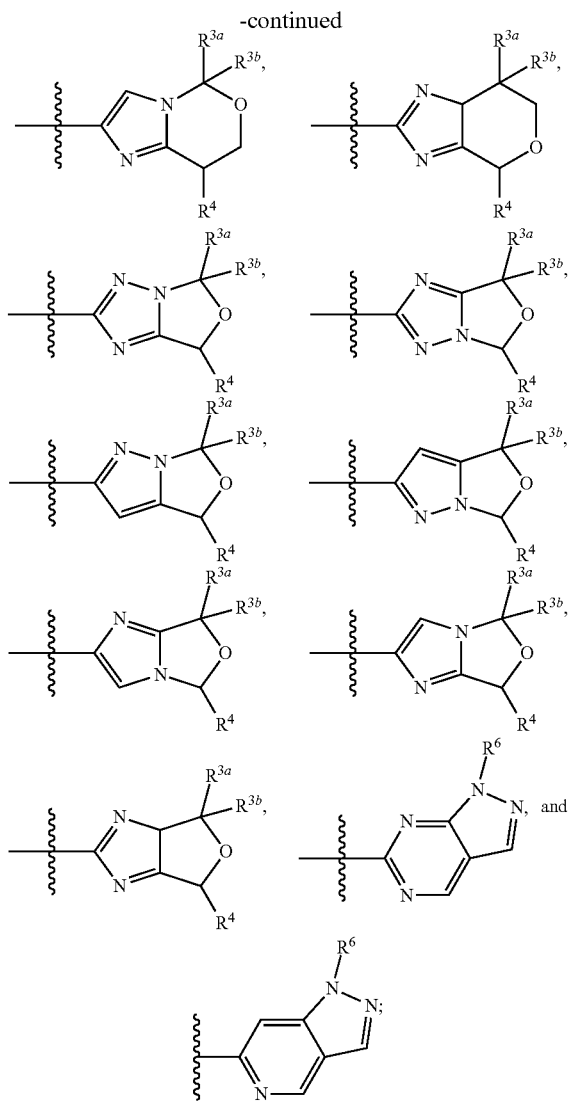

wherein:
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or
each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN; or
$R^{3a}$ and $R^{3b}$, together with the carbon atom to which they are both attached, form 1,1-cyclopropylene;
$R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano; and
$R^6$ is selected from the group consisting of H, $C_1$-$C_6$ alkyl, $C_1$-$C_6$ haloalkyl, and $C_3$-$C_6$ cycloalkyl.

3. The compound of claim 2, or a pharmaceutically acceptable salt thereof, wherein the A ring and the B ring together are:

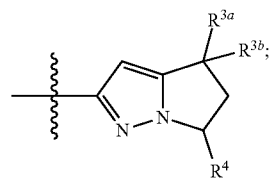

wherein:
$R^{3a}$ and $R^{3b}$ are selected as follows:
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or
each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN; or
$R^{3a}$ and $R^{3b}$, together with the carbon atom to which they are both attached, form 1,1-cyclopropylene; and
$R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

4. The compound of claim 2, or a pharmaceutically acceptable salt thereof, wherein the A ring and the B ring together are selected from the group consisting of:

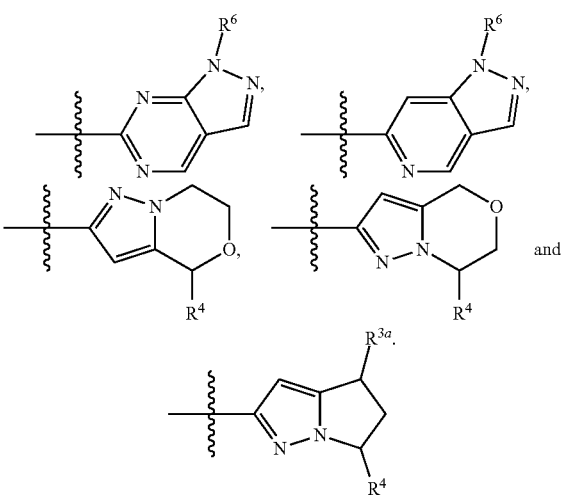

5. The compound of claim 4, or a pharmaceutically acceptable salt thereof, wherein the A ring and the B ring together are selected from the group consisting of:

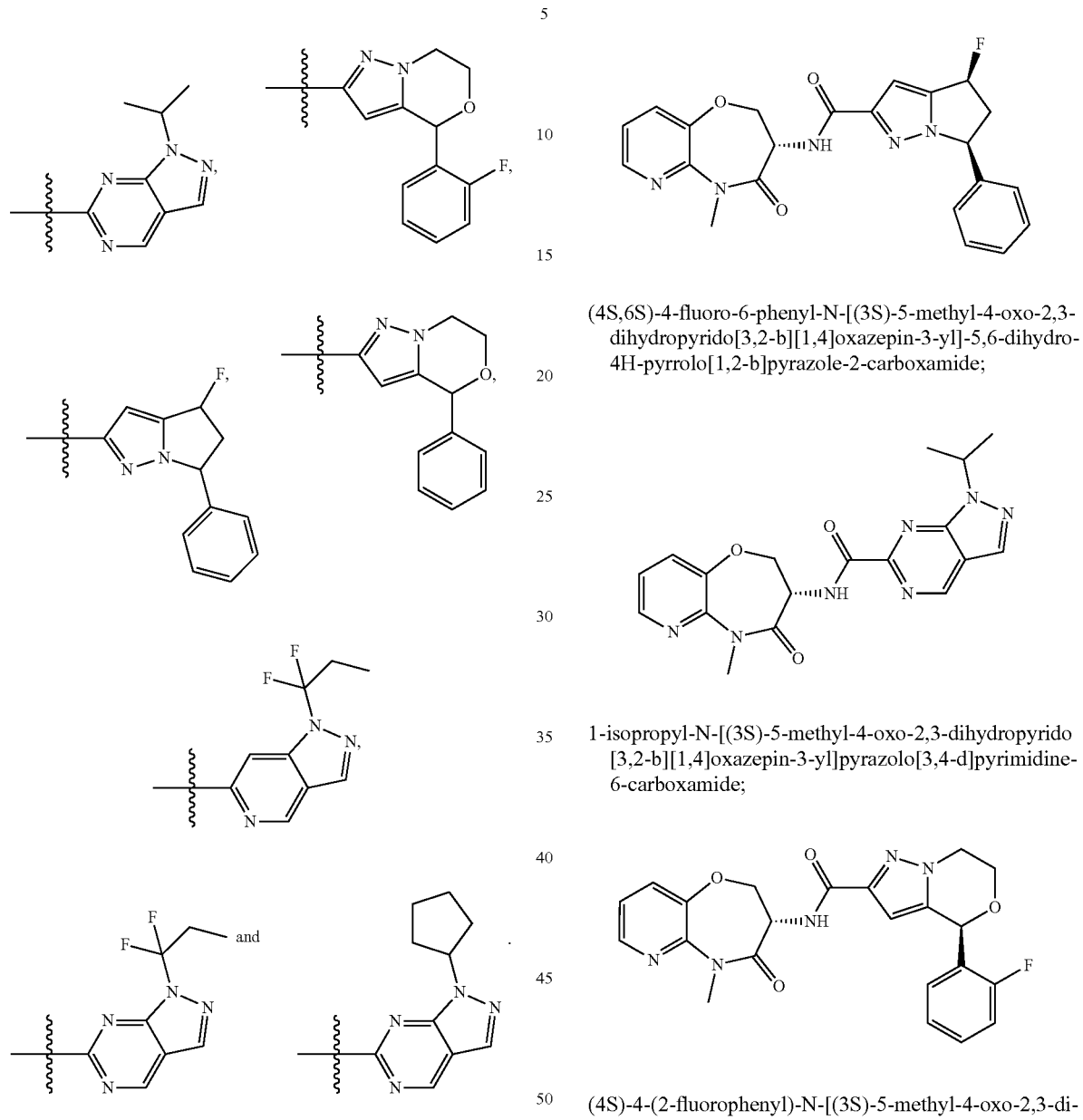

11. The compound of claim 1, or a pharmaceutically acceptable salt thereof, wherein the compound is selected from the group consisting of:

(4S,6S)-4-fluoro-6-phenyl-N-[(3S)-5-methyl-4-oxo-2,3-dihydropyrido[3,2-b][1,4]oxazepin-3-yl]-5,6-dihydro-4H-pyrrolo[1,2-b]pyrazole-2-carboxamide;

1-isopropyl-N-[(3S)-5-methyl-4-oxo-2,3-dihydropyrido[3,2-b][1,4]oxazepin-3-yl]pyrazolo[3,4-d]pyrimidine-6-carboxamide;

(4S)-4-(2-fluorophenyl)-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide;

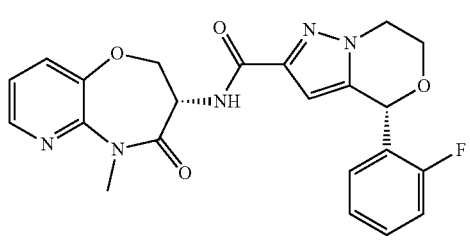 [SMILES: CN1C(=O)[C@@H](NC(=O)c2cc3n(n2)CCO[C@@H]3c2ccccc2F)COc2cccnc21]

6. The compound of claim 1, or a pharmaceutically acceptable salt thereof, wherein X is O or CH$_2$.

7. The compound of claim 1, or a pharmaceutically acceptable salt thereof, wherein R$^1$ is methyl or CD$_3$.

8. The compound of claim 1, or a pharmaceutically acceptable salt thereof, wherein R$^2$ is selected from the group consisting of hydrogen, deutero, halogen, cyano, C$_1$-C$_6$ alkyl, C$_1$-C$_6$ haloalkyl, C$_3$-C$_6$ cycloalkyl, C$_1$-C$_6$ alkoxy, C$_1$-C$_6$ haloalkoxy, C$_1$-C$_6$ thioalkyl, cyano, phenyl, and benzyl.

9. The compound of claim 1, or a pharmaceutically acceptable salt thereof, wherein n is 0.

10. The compound of claim 1, or a pharmaceutically acceptable salt thereof, wherein R$^{7a}$ and R$^{7b}$ are each independently selected from the group consisting of H and C$_1$-C$_6$ alkyl.

(R)-4-(2-fluorophenyl)-N—((S)-5-methyl-4-oxo-2,3,4,5-tetrahydropyrido[3,2-b][1,4]oxazepin-3-yl)-6,7-dihydro-4H-pyrazolo[5,1-c][1,4]oxazine-2-carboxamide;

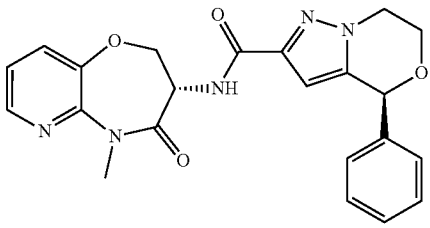 [SMILES: CN1C(=O)[C@@H](NC(=O)c2cc3n(n2)CCO[C@H]3c2ccccc2)COc2cccnc21]

(4S)-4-phenyl-N-[(3S)-5-methyl-4-oxo-2,3-dihydropyrido[3,2-b][1,4]oxazepin-3-yl]-6,7-dihydro-4H-pyrazolo[5,1-c][1,4]oxazine-2-carboxamide;

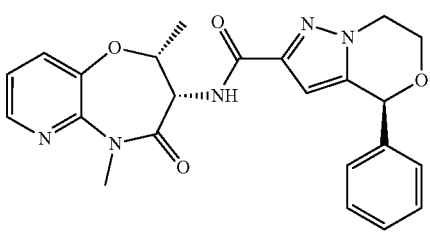 [SMILES: C[C@H]1Oc2cccnc2N(C)C(=O)[C@H]1NC(=O)c1cc2n(n1)CCO[C@H]2c1ccccc1]

(4S)-4-phenyl-N-[(2R,3S)-2,5-dimethyl-4-oxo-2,3-dihydropyrido[3,2-b][1,4]oxazepin-3-yl]-6,7-dihydro-4H-pyrazolo[5,1-c][1,4]oxazine-2-carboxamide;

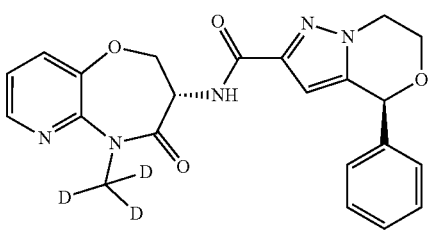 [SMILES: [2H]C([2H])([2H])N1C(=O)[C@@H](NC(=O)c2cc3n(n2)CCO[C@H]3c2ccccc2)COc2cccnc21]

(4S)-4-phenyl-N-[(3S)-4-oxo-5-(trideuteriomethyl)-2,3-dihydropyrido[3,2-b][1,4]oxazepin-3-yl]-6,7-dihydro-4H-pyrazolo[5,1-c][1,4]oxazine-2-carboxamide;

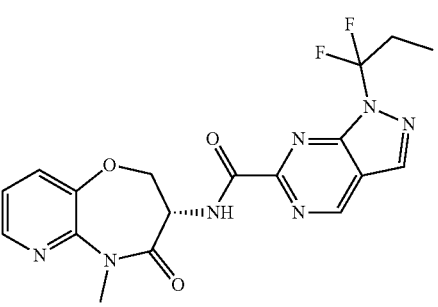 [SMILES: CCC(F)(F)n1ncc2cnc(C(=O)N[C@H]3COc4cccnc4N(C)C3=O)nc21]

1-(1,1-difluoropropyl)-N-[(3S)-5-methyl-4-oxo-2,3-dihydropyrido[3,2-b][1,4]oxazepin-3-yl]pyrazolo[3,4-d]pyrimidine-6-carboxamide;

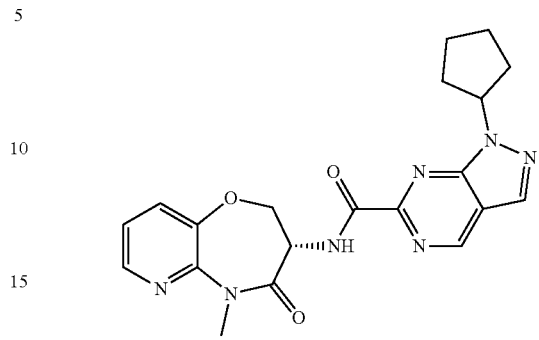

1-cyclopentyl-N-[(3S)-5-methyl-4-oxo-2,3-dihydropyrido[3,2-b][1,4]oxazepin-3-yl]pyrazolo[3,4-d]pyrimidine-6-carboxamide;

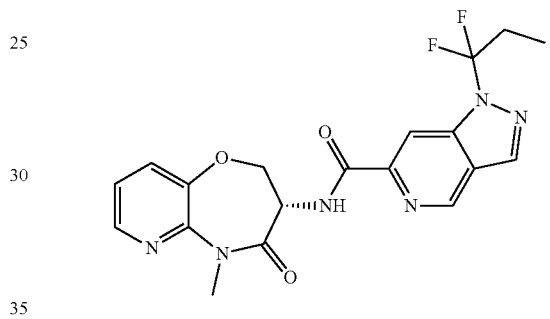

1-(1,1-difluoropropyl)-N-[(3S)-5-methyl-4-oxo-2,3-dihydropyrido[3,2-b][1,4]oxazepin-3-yl]pyrazolo[4,3-c]pyridine-6-carboxamide.

12. The compound of claim 11, or a pharmaceutically acceptable salt thereof, having a RIP1 kinase inhibitory activity $K_i$ of less than 100 nM.

13. A pharmaceutical composition comprising a compound of claim 1, or a pharmaceutically acceptable salt thereof, and a pharmaceutically acceptable carrier.

14. A method for the therapeutic treatment of a disease or disorder in a human, the method comprising administering to the human in-need thereof an effective amount of a compound of claim 1, or a pharmaceutically acceptable salt thereof, wherein the disease or disorder is selected from the group consisting of Parkinson's disease, Lewy body dementia, multiple system atrophy, Parkinson-plus syndrome, tauopathy, Alzheimer's disease, frontotemporal dementia, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathy, progressive supranuclear palsy, corticobasal degeneration, and demyelinating disease.

15. The method of claim 14, wherein the disease or disorder is Alzheimer's disease.

16. The method of claim 14, wherein the disease or disorder is multiple sclerosis.

17. The method of claim 14, wherein the disease or disorder is Parkinson's disease.

18. The method of claim 14, wherein the disease or disorder is amyotrophic lateral sclerosis.

19. The method of claim 14, wherein the disease or disorder is Huntington's disease.

20. The method of claim 14, wherein the disease or disorder is spinal muscular atrophy.

21. A method for the therapeutic treatment of a disease or disorder in a human, the method comprising administering to the human in need thereof an effective amount of a compound of claim 1, or a pharmaceutically acceptable salt thereof, wherein the disease or disorder is selected from the group consisting of irritable bowel disorder (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatitis, psoriasis, retinitis pigmentosa, retinal degeneration, chronic kidney disease, acute respiratory distress syndrome (ARDS), and chronic obstructive pulmonary disease (COPD).

22. The method of claim 21, wherein the disease or disorder is irritable bowel disorder (IBD).

\* \* \* \* \*